(12) United States Patent
Yuan et al.

(10) Patent No.: US 10,689,413 B2
(45) Date of Patent: Jun. 23, 2020

(54) COMPOSITION ENRICHED IN SINGLE ISOMER OF NUC-1031 AND PREPARATION METHOD AND USE THEREOF

(71) Applicant: BrightGene Bio-Medical Technology Co., Ltd., Suzhou, Jiangsu (CN)

(72) Inventors: Jiandong Yuan, Suzhou (CN); Yangqing Huang, Suzhou (CN); Linfeng Miao, Suzhou (CN); Jianing Gu, Suzhou (CN); Chaohua Liang, Suzhou (CN); Zhengye Wang, Suzhou (CN); Zhanli Sun, Suzhou (CN)

(73) Assignee: BrightGene Bio-Medical Technology Co., Ltd., Jiangsu (CN)

( * ) Notice: Subject to any disclaimer, the term of this patent is extended or adjusted under 35 U.S.C. 154(b) by 0 days.

(21) Appl. No.: 15/754,009

(22) PCT Filed: Sep. 13, 2016

(86) PCT No.: PCT/CN2016/098847
§ 371 (c)(1),
(2) Date: Feb. 21, 2018

(87) PCT Pub. No.: WO2017/045583
PCT Pub. Date: Mar. 23, 2017

(65) Prior Publication Data
US 2018/0244710 A1    Aug. 30, 2018

(30) Foreign Application Priority Data
Sep. 16, 2015  (CN) .......................... 2015 1 0586447

(51) Int. Cl.
  *C07H 19/10*   (2006.01)
  *A61K 31/7068*  (2006.01)
  *C07H 1/02*    (2006.01)
  *A61P 35/00*   (2006.01)

(52) U.S. Cl.
  CPC ......... *C07H 19/10* (2013.01); *A61K 31/7068* (2013.01); *A61P 35/00* (2018.01); *C07H 1/02* (2013.01)

(58) Field of Classification Search
  CPC ..... A61K 31/7068; A61P 35/00; C07H 19/10; C07H 19/06
  See application file for complete search history.

(56) References Cited

U.S. PATENT DOCUMENTS

| | | | | |
|---|---|---|---|---|
| 8,618,076 B2* | 12/2013 | Ross | ...................... | A61P 31/14 514/51 |
| 8,642,756 B2* | 2/2014 | Ross | ...................... | C07H 1/00 536/26.8 |
| 8,735,569 B2* | 5/2014 | Ross | .................. | A61K 31/7072 536/25.33 |
| 8,841,275 B2* | 9/2014 | Du et al. | ............ | A61K 31/7076 514/45 |
| 8,859,756 B2* | 10/2014 | Ross | ...................... | A61P 31/14 536/26.1 |
| 9,156,874 B2* | 10/2015 | Chang | .................. | C07F 9/65586 |
| 9,284,342 B2* | 3/2016 | Ross | ..................... | C07F 9/2479 |
| 9,370,569 B2* | 6/2016 | Smith | .................. | A61K 31/708 |
| 9,834,577 B2* | 12/2017 | Dammalapati et al. | ..................... | C07H 1/02 |
| 10,030,044 B2* | 7/2018 | Dousson | ................ | C07H 19/20 |
| 10,092,649 B2* | 10/2018 | Smith | .................. | C07H 19/213 |
| 10,117,888 B2 | 11/2018 | Griffith et al. | | |
| 2011/0245484 A1 | 10/2011 | Ross et al. | | |
| 2011/0251152 A1 | 10/2011 | Ross et al. | | |
| 2013/0288997 A1 | 10/2013 | Ross et al. | | |

(Continued)

FOREIGN PATENT DOCUMENTS

| | | |
|---|---|---|
| AU | 2015278899 | 12/2015 |
| AU | 2015278900 | 12/2015 |
| WO | 2005012327 | 2/2005 |

(Continued)

OTHER PUBLICATIONS

Magdalena Slusarczyk, et al., Application of ProTide Technology to Gemcitabine: A Successful Approach to Overcome the Key Cancer Resistance Mechanisms Leads to a New Agent (NUC-1031) in Clinical Development, Journal of Medicinal Chemistry, Jan. 28, 2014, pp. 1531-1542.
International Search Report dated Nov. 15, 2016 in corresponding application No. PCT/CN2016/098847.
ISA/CN, International Search Report for PCT/CN2016/098845 (dated Dec. 9, 2016).
ISA/CN, International Search Report for PCT/CN2016/098846 (dated Nov. 30, 2016).
AU Office Action in Australian Appln. No. 2016322374, dated Feb. 12, 2020, 5 pages.
AU Office Action in Australian Appln. No. 2016322375, dated Feb. 4, 2020, 3 pages.
Third Party Observations dated Jan. 22, 2020.
Third Party Observations dated Jan. 30, 2020.

(Continued)

*Primary Examiner* — Lawrence E Crane
(74) *Attorney, Agent, or Firm* — Fish & Richardson P.C.

(57) ABSTRACT

Provided is a preparation method of a composition enriched in compound $S_p$-1. The method performs isomer separation on a reaction product from the first step, and then performs a two-step chemical synthesis, so as to prepare a composition comprising high-purity compound $S_p$-1, wherein the HPLC purity of the single isomer $S_p$-1 is 90% or more. Provided is a composition enriched in compound $S_p$-1. The composition has an inhibitory effect on tumor cell proliferation in vitro significantly higher than that of NUC-1031 and compound $R_p$-1. Also provided are the use of the composition, and a pharmaceutical composition comprising the composition and at least one pharmaceutically acceptable excipient.

10 Claims, 10 Drawing Sheets

(56) References Cited

U.S. PATENT DOCUMENTS

2017/0107246 A1* 4/2017 Griffith .................. A61P 7/00
2017/0226147 A1* 8/2017 Griffith .................. A61P 35/00

FOREIGN PATENT DOCUMENTS

| WO | WO 2011/123645 | 10/2011 |
| --- | --- | --- |
| WO | WO 2012/012465 | 1/2012 |
| WO | 2012075140 | 6/2012 |
| WO | WO 2013/187978 | 12/2013 |
| WO | WO 2014/033617 | 3/2014 |
| WO | WO 2014/058801 | 4/2014 |
| WO | 2014076490 | 5/2014 |
| WO | WO 2014/076490 | 5/2014 |
| WO | WO 2015/198058 | 12/2015 |
| WO | WO 2016/055769 | 4/2016 |
| WO | WO 2016055769 | 4/2016 |

OTHER PUBLICATIONS

Letter From Outside Counsel dated Dec. 11, 2019.
Ross et al., "Synthesis of Diastereomerically Pure Nucleotide Phosphoramidates," J. Org. Chem., 2011, 76:8311-8319.

* cited by examiner

Table of Peaks

PDA Ch2 220nm

| Peak# | Name | Retention time | Area | Peak height | Area % | Theoretical plates | Resolution | Tailing factor |
|---|---|---|---|---|---|---|---|---|
| 1 | | 15.720 | 32073 | 3645 | 1.40 | 64293 | 0.0 | 1.1 |
| 2 | | 17.879 | 7237 | 1012 | 0.32 | 118523 | 9.5 | 1.0 |
| 3 | 61501e | 26.247 | 599792 | 86409 | 26.25 | 276259 | 41.1 | 1.1 |
| 4 | 61501b | 26.655 | 1645757 | 235596 | 72.03 | 281184 | 2.0 | 1.1 |
| Total | | | 2284859 | 326662 | 100.00 | | | |

COMPOSITION ENRICHED IN SINGLE ISOMER OF NUC-1031 AND PREPARATION METHOD AND USE THEREOF

CROSS-REFERENCES TO RELATED APPLICATIONS

This application is a U.S. national stage application of PCT International Application No. PCT/CN2016/098847 filed on Sep. 13, 2016, which claims the benefit of foreign priority of Chinese patent application No. 201510586447.6 filed on Sep. 16, 2015, the contents of all of which are incorporated herein by reference.

This subject matter of this application is related to co-pending U.S. patent application Ser. No. 15/753,734 filed on Feb. 20, 2018, and co-pending U.S. patent application Ser. No. 15/754,318 filed on Feb. 22, 2018, both of which are also incorporated herein by reference in their entirety.

TECHNICAL FIELD

The present disclosure relates to a composition enriched in the single isomer of NUC-1031 and a preparation method thereof, and also relates to the use of the composition and a pharmaceutical composition comprising this composition and at least one pharmaceutically acceptable excipient. The present disclosure also relates to the compound $S_p$-1 in crystalline form and a preparation method thereof.

BACKGROUND

NUC-1031 is a prodrug of gemcitabine developed by NuCana BioMed Ltd., and is currently in Phase II clinical trials for the treatment of cancers such as advanced solid tumors, pancreatic cancer and breast cancer. The CAS of NUC-1031 is 840506-29-8 and NUC-1031 has a structure represented by the following formula 1, including two single isomers, $R_p$-1 and $S_p$-1:

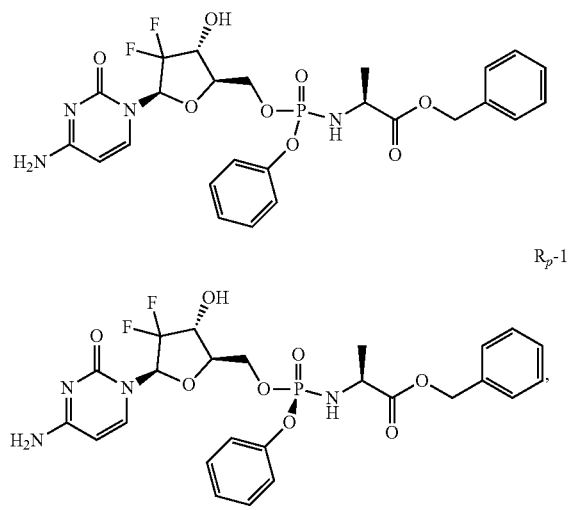

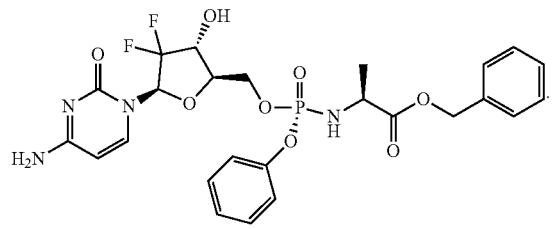

On page 70 in the description of WO2005012327 are disclosed the specific structure of NUC-1031 and the preparation method thereof, the method comprising, specifically, in the presence of NMI, reacting gemcitabine with benzyl-(benzoyl-L-alanine)-chlorophosphate at a molar ratio of 1:3 for 2 hours, with THF/pyridine as the solvent, to give a crude product, which is then subjected to separation and purification on a silica gel column, and eluted with dichloromethane/methanol (95:5) to give a foamy solid with a yield of only 16%.

WO2014076490A1 discloses the following method for preparing NUC-1031,

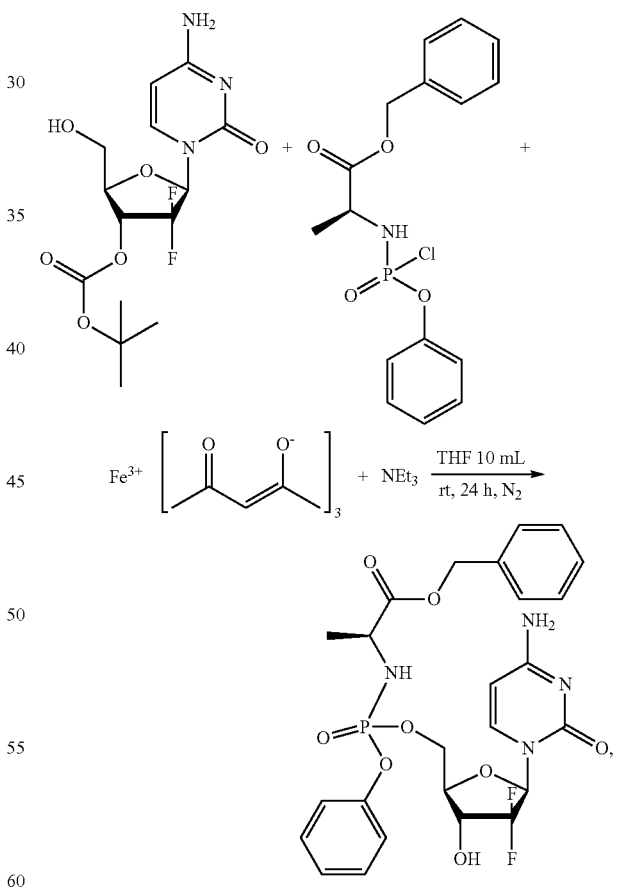

3'-Boc-protected gemcitabine (100 mg) is reacted with 2 mol equivalents of phenyl(benzyl-L-alanine)chlorophosphate (150 mg), with 0.5 mol equivalents of tris(acetylacetone)Fe(III) (56 mg) as the catalyst, 1.5 mol equivalents of DIPEA (55 μL) as the base, and 10 ml of THF as the solvent; the reaction is conducted at room temperature under the protection of nitrogen gas for 24 hours with a yield of 45%, wherein the ratio of the isomers, i.e., $R_p:S_p$ is 3:1.

A literature entitled "Application of ProTide Technology to Gemcitabine: A Successful Approach to Overcome the Key Cancer Resistance Mechanisms Leads to a New Agent (NUC-1031) in Clinical Development" (*Journal of Medicinal Chemistry*, Volume 57, Issue 4, Pages 1531-1542) reported a method for preparing NUC-1031 by deprotecting the hydroxyl group of the compound 5f represented by the following formula in the presence of TFA with dichloromethane as the solvent and finally by purification on a silica gel column, the yield is 70%, the contents of the isomers are 48% and 52%, respectively.

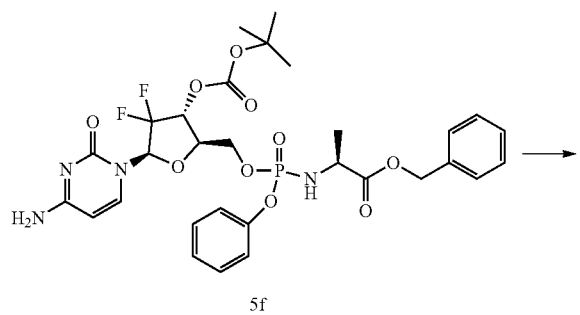

5f

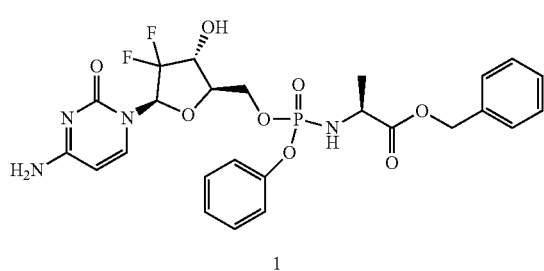

1

At present, the preparation method of the single isomer of NUC-1031 has not been reported in the prior art. Since the two enantiomers of the chiral P in the molecular structure of NUC-1031 are very similar in structure and polarity, it becomes very difficult to isolate a high-purity single isomer from the racemic mixture of NUC-1031, and in particular, it is even more difficult to balance purity and yield simultaneously in the purification process. The inventors have attempted to purify NUC-1031 by various conventional methods in the art such as crystallization, silica gel column chromatography, as well as reversed phase C18 silica gel-bonded preparative chromatography, normal phase preparative chromatography with spherical silica based packing, and chiral chromatographic separation, but all of them can hardly isolate a single isomer with a purity of not less than 90%.

It is known in the art that usually when a chiral compound is used as a drug, the relationship between the configuration and the pharmacological effect of the isomer can be divided into the following scenarios: (1) the pharmacological effect of the drug is completely or mainly generated by one of the enantiomers, for example, (S)-naproxen has an analgesic effect 35 times stronger than that of the R isomer; (2) the two isomers have completely opposite pharmacological effects, for example, the dextrorotatory isomer of Picenadol is an opiate receptor agonist, while the levorotatory isomer thereof is an opiate receptor antagonist; (3) an isomer arises serious adverse reactions, for example, the emetic reaction of the anthelmintic tetramisole is caused by the dextrorotatory isomer thereof; (4) one pharmacological effect has high stereoselectivity, while the other pharmacological effects have low or no stereoselectivity, for example, addiction to the antitussive methorphan is mainly caused by the levorotatory isomer thereof, but in terms of the antitussive effect, the dextrorotatory isomer and the levorotatory isomer have the same intensity; and (5) the two enantiomers have different pharmacological effects, but the combination use is beneficial, for example, the dextrorotatory isomer of the antihypertensive nehivolol is a β-receptor blocker, while the levorotatory isomer thereof can reduce peripheral vascular resistance and has protective effect for heart.

It is known that NUC-1031 molecule contains many chiral atoms, and isolating single isomers from NUC-1031, studying their biological activities respectively, and studying the pharmacological effects, toxic side effects or adverse reactions of NUC-1031 to develop similar drugs with better activity and less toxic side effects will be of great significance. Preparing high-purity single isomers that meet the needs of clinical research and screening the single isomer that plays an important role in the pharmacological activity of NUC-1031 are still problems that need to be solved in the art at present.

SUMMARY

In order to solve the above problems, in the first aspect, the present disclosure provides a composition enriched in compound $S_p$-1;

In the second aspect, the present disclosure provides a method for preparing the composition;

In the third aspect, the present disclosure provides the use of the composition in the preparation of a drug for the treatment of cancer;

In the fourth aspect, the present disclosure also provides a pharmaceutical composition comprising the composition.

In the fifth aspect, the present disclosure also provides the compound $S_p$-1 in crystalline form and the preparation method thereof.

In the first aspect, the present disclosure provides the composition enriched in compound $S_p$-1, wherein the purity of the compound $S_p$-1 in said composition is not less than 90%, the term "purity" refers to the weight percentage of the compound $S_p$-1 in said composition, and the weight ratio of the compound $S_p$-1 to the compound $R_p$-1 in said composition is not less than 90:10, $R_p$-1

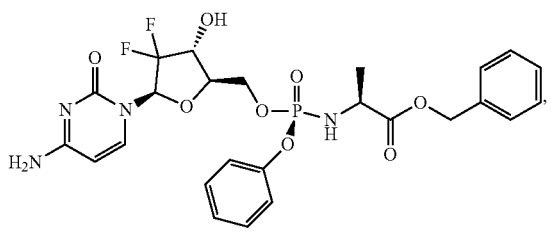

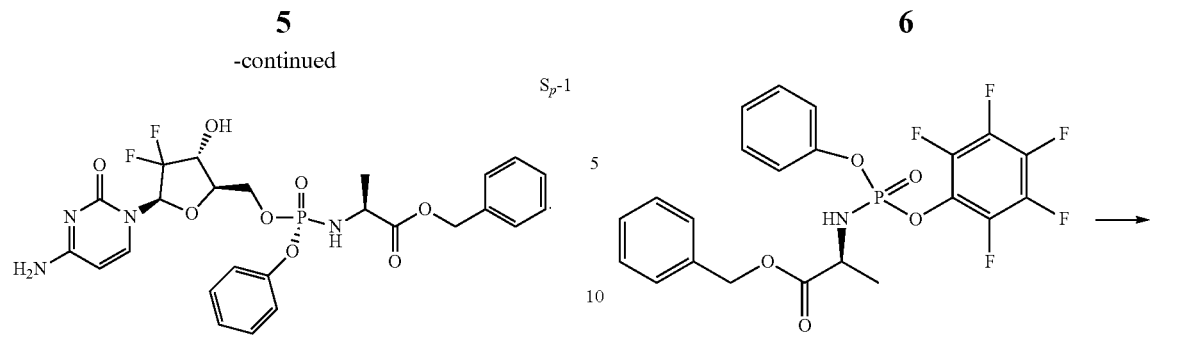

Further, in said composition, the purity of the compound $S_p$-1 is not less than 97%, and the weight ratio of the compound $S_p$-1 to the compound $R_p$-1 in the composition is not less than 97:3.

Still further, in said composition, the purity of the compound $S_p$-1 is not less than 99%, and the weight ratio of the compound $S_p$-1 to the compound $R_p$-1 in the composition is not less than 99:1.

In the second aspect, the present disclosure provides a method for preparing any of the above compositions, said method comprising the following steps:

(1) reacting a compound 61501h with a compound 61501g under alkaline conditions, and then reacting with a compound 61501f to prepare a compound 61502:

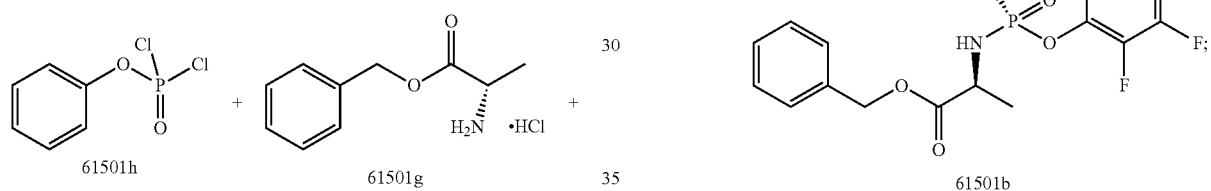

(2) isolating a compound 61501b by crystallization of the compound 61502:

(3) reacting the compound 61501b with a compound 61501c to prepare a compound 61501a:

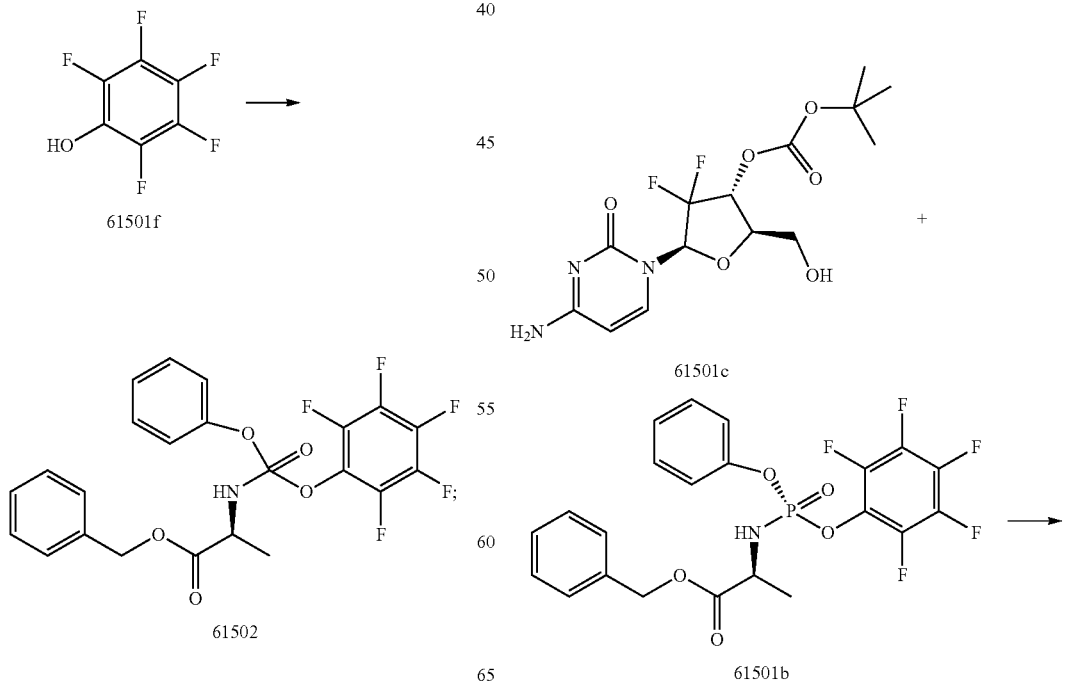

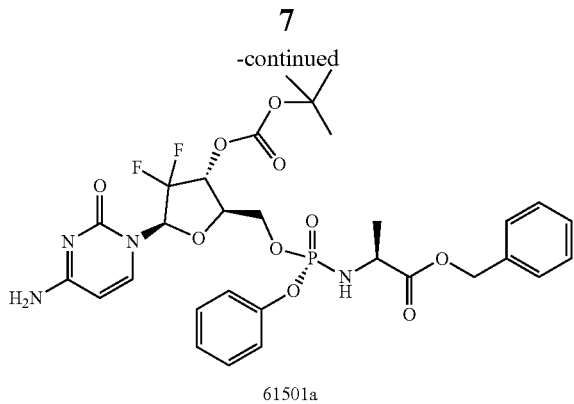

61501a (4) deprotecting the hydroxyl protecting group of the compound 61501a to obtain the composition enriched in compound $S_p$-1:

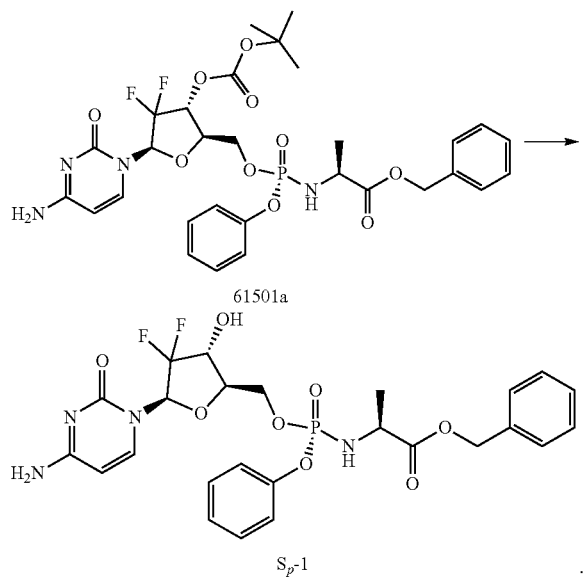

$S_p$-1

In the above method, in the step (1), the reaction is preferably carried out under the atmosphere of $N_2$, the compound 61501h is added to a suitable solvent (such as dichloromethane, isopropanol, DMF and dioxane), and then the compound 61501g and a suitable base (such as triethylamine, DIPEA, NMM, pyridine and piperidine) are added at a suitable temperature (preferably −80° C.); after the dropwise addition is complete, it is preferred that the reaction is carried out at room temperature overnight and then, to the reaction solution, the compound 61501f and a suitable base (such as triethylamine, DIPEA, NMM, pyridine and piperidine) are added; after the reaction is complete, the solvent is removed by distillation, ethyl acetate and water are added for extraction, and the target compound 61502 is obtained by separation.

In the step (2), the compound prepared in the step (1) is further crystallized and separated to obtain the isomer 61501b; the preferred crystallization solvent is ethyl acetate and petroleum ether; and further preferably, the compound 61502 is added to ethyl acetate, the mixture is stirred, then petroleum ether is added dropwise and slowly to the mixture, and crystals precipitate, thereby obtaining the target compound 61501b; wherein the weight-to-volume ratio of the compound 61502 to ethyl acetate is preferably 2:5 to 4:5, in said weight-to-volume ratio, the unit of weight is gram and the unit of volume is milliliter, and the volume ratio of ethyl acetate to petroleum ether is 1:4 to 1:6 or 1:3.

In the above step (3), it is preferred that under the atmosphere of nitrogen gas, a Grignard reagent (such as tert-butylmagnesium chloride, and preferably a solution of tert-butylmagnesium chloride in tetrahydrofuran) is added to the compound 61501c in a suitable solvent (such as tetrahydrofuran, dichloromethane) under the conditions of a suitable temperature (such as −10° C. to 5° C., and preferably 0° C.) to react for about 0.5 to 3 hours; thereafter, the compound 61501b obtained by separation in the step (2) is added for reaction, and till the reaction is complete, water is added to the reaction solution; then ethyl acetate is used for extraction to give the crude compound 61501a; the above crude product can be further purified by a conventional method such as crystallization, column chromatography, and the like, and it is preferred to perform purification using silica gel column chromatography with dichloromethane-methanol as an eluent.

In the above step (4), it is preferred that under the protection of nitrogen gas, the hydroxyl protecting group of the compound 61501a is deprotected by catalysis in a suitable solvent (such as dichloromethane, ethyl acetate) using an acid (such as trifluoroacetic acid, hydrogen chloride/ethyl acetate) under the conditions of a suitable temperature (such as −10° C. to 5° C., and preferably 0° C.); after the reaction is complete, an aqueous solution of weak base (such as a saturated sodium bicarbonate solution) and an organic solvent (such as ethyl acetate) are added, the organic layer is separated, concentrated and dried to give the crude compound $S_p$-1; and it is further preferred to purify the above crude product, for example, by using silica gel column chromatography with dichloromethane-methanol as an eluent.

Further, said compound 61501c in the above step (3) of the method is prepared from a compound 61501d:

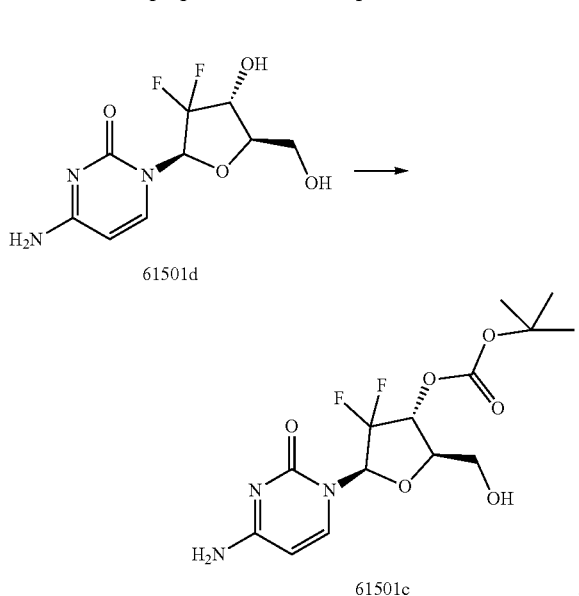

Further, it is preferred that the compound 61501c is prepared by reacting the compound 61501d with di-tert-butyl dicarbonate in a suitable solvent (such as tetrahydrofuran, dichloromethane, isopropanol or a mixed solution thereof with water) under alkaline (such as sodium carbonate, sodium bicarbonate, and the like) conditions.

In the third aspect, the present disclosure provides the use of the above composition, which is used in the preparation of a drug for the treatment of cancer; further, said cancer includes pancreatic cancer, advanced solid tumors, ovarian tumor, non-small cell lung cancer, breast cancer, bladder cancer, cervical cancer, mesothelioma, esophageal cancer, gastric cancer, colorectal cancer, liver cancer, cholangiocarcinoma, nasopharyngeal cancer, testicular cancer, lymphoma, or head and neck cancer; and more preferably, said cancer includes pancreatic cancer, advanced solid tumors, ovarian tumor, and breast cancer.

In the fourth aspect, the present disclosure also provides the pharmaceutical composition comprising the composition, said pharmaceutical composition comprises the composition enriched in compound $S_p$-1 provided by the present disclosure and at least one pharmaceutically acceptable excipient.

Said pharmaceutical composition can be administered orally or parenterally, including intravenously, subcutaneously, intraperitoneally, intramuscularly, by inhalation, rectally, and topically (such as buccally or sublingually).

Among them, pharmaceutical compositions for oral administration include tablets, capsules, granules or suspensions; the tablets for oral administration comprise the composition provided by the present disclosure as an active ingredient, and may further comprise one or more pharmaceutically acceptable excipients, such as diluent, disintegrant, binder, lubricant, sweetener, flavoring agent, pigment and preservative. When corn starch and alginic acid are used as disintegrants, suitable inert diluents include sodium carbonate, calcium carbonate, sodium phosphate, calcium phosphate and lactose. The binders include starch and gelatin, and optionally, the lubricant is magnesium stearate, stearic acid or talc. Optionally, said tablets may also be coated with glycerol monostearate or glycerol distearate to delay the absorption in stomach.

The capsules for oral administration include hard capsules and soft capsules, wherein the hard capsules comprise the pharmaceutical composition provided by the present disclosure as the effective active ingredient and a solid diluent; and the soft capsules comprise the pharmaceutical composition provided by the present disclosure as the effective active ingredient, and water or oil (such as peanut oil, liquid paraffin or olive oil).

The dosage form for rectal administration is suppository, wherein the base of the suppository may be cocoa butter or salicylate.

The forms of the formulations for vaginal administration include pessaries, tampons, creams, gels, pastes, foams, or sprays, wherein said formulations comprise a pharmaceutical composition containing the active ingredient and a conventional carrier known in the art.

When used in the dosage forms for intravenous injection, intraperitoneal administration, subcutaneous administration and intramuscular administration, the pharmaceutical composition provided by the present disclosure is usually sterile solution or sterile suspension, and has suitable pH value and osmotic pressure. Such formulations can be prepared and obtained according to the conventional methods generally known in the art.

The administration dosage of said pharmaceutical composition is 0.1 to 300 mg/kg body weight/day; preferably 0.5 mg/kg body weight/day; and a further preferred suitable administration dosage is 1 to 50 mg/kg body weight/day, and more preferably 1 to 50 mg/kg body weight/day. Preferably, the composition is administered twice, three times, four times, or five times a day at intervals. The composition preferably comprises 10 to 1500 mg of the active ingredient, more preferably 20 to 1000 mg of the active ingredient, and most preferably 50 to 700 mg of the active ingredient as one dosage unit.

In another aspect, the present disclosure provides the compound $S_p$-1 in crystalline form, in particular to the substantially pure crystalline form. Preferably, the crystalline form is wherein it does not contain or substantially does not contain water. Further, said compound $S_p$-1 in crystalline form has unit cell dimensions: a=11.36 Å, b=34.84 Å, c=15.12 Å, and the volume is 5554 Å$^3$. In order to facilitate the identification of the new crystalline form, the present disclosure provides the data of X-ray diffraction analysis and the conditions used for obtaining these data as follows:

| | |
|---|---|
| Temperature | 123(2) K |
| Wavelength | 0.71073 Å |
| Crystal system, space group | Monoclinic, P2$_1$ |
| Unit cell dimensions | a = 11.3607(19) Å |
| | b = 34.841(5) Å |
| | c = 15.118(2) Å |
| | α = 90° |
| | β = 111.857(4)° |
| | γ = 90° |
| Volume | 5551.8(15) Å$^3$ |
| Z | 8 |
| Calculated density | 1.388 Mg/m$^3$ |
| Absorption coefficient | 0.166 mm$^{-1}$ |
| F (000) | 2416 |
| Crystal size | 2.26 × 0.26 × 0.23 mm |
| θ Range of data collection | 1.97° to 27.63° |
| Reflections collected/unique | 123782/13011[R(int) = 0.1357] |
| Completeness | 98.9% |
| Refinement method | Full-matrix least-squares on F$^2$ |
| Data/restraints/parameters | 13011/3/1403 |
| Goodness-of-fit on F$^2$ | 1.858 |
| Final R indices [(I > 2sigma(I))] | R$_1$ = 0.1853, wR$_2$ = 0.4314 |
| Largest diff. peak and hole | 1.575 and −1.177e.A$^{-3}$ |

The compound $S_p$-1 in crystalline form can be prepared in such manner: adding the compound $S_p$-1 prepared by the aforementioned method or the methods mentioned in specific Examples of the present disclosure to a solvent, such as a solvent composed of a lower alcohol and water, and decreasing the temperature of the system from 30 to 50° C. slowly to 0 to 5° C. to obtain a rod-shaped single crystal. Preferably, said lower alcohol is a C$_{1-3}$ alcohol (such as methanol, ethanol, propanol or isopropanol), and more preferably, said lower alcohol is ethanol; wherein the amount ratio of the lower alcohol to water is preferably 1:3 (v/v).

In another aspect, the present disclosure also provides a pharmaceutical composition comprising said compound $S_p$-1 in crystalline form and at least one pharmaceutically acceptable excipient. The compound $S_p$-1 in crystalline form can be used in the same indications as those known to be treated with NUC-1031, such as pancreatic cancer, advanced solid tumors, ovarian tumor, non-small cell lung cancer, breast cancer, bladder cancer, cervical cancer, mesothelioma, esophageal cancer, gastric cancer, colorectal cancer, liver cancer, cholangiocarcinoma, nasopharyngeal cancer, testicular cancer, lymphoma, head and neck cancer, or the like. The pharmaceutical composition comprising said compound $S_p$-1 in crystalline form and at least one pharmaceutically acceptable excipient may be administered via any conventional route, for example, oral administration (such as tablets or capsules), or nasal or pulmonary administration (inhalation) and so on.

The composition enriched in compound $S_p$-1 provided by the present disclosure shows relatively strong cytotoxic effect on BxPC-3, MIA PaCa-2 and OVCAR-3 tumor cells, and has $IC_{50}$ values between about 0.01 nM and 0.05 nM; its inhibitory effect on the proliferation activity of tumor cells in vitro is about 10 times that of the compound. $R_p$-1; and the composition enriched in compound $S_p$-1 provided by the present disclosure has better in vivo antitumor activity as compared with gemcitabine and the compound $R_p$-1. The results of the pharmacokinetic evaluation show that the concentration of the active metabolite dFdCTP of the composition enriched in compound $S_p$-1 provided by the present disclosure is significantly higher than that of the compound $R_p$-1 in tumor tissues.

Secondly, in the composition provided by the present disclosure, the diastereoisomeric $S_p$-1 is highly enriched, which provides starting material for conducting further clinical research on the pharmacological activity of NUC-1031 and developing new anticancer drugs with good activity and low side effects in the future. Besides, the inventor inventively carries out the separation of the single isomers right after the completion of the first-step reaction, which significantly saves the starting material as compared with the prior art that isolates the single isomers from racemic mixtures and/or racemates. Meanwhile, the separation of the isomers in the first-step reaction adopts the crystallization method, the operation of which is convenient, and said method greatly saves costs as compared with the prior art that uses chiral chromatographic column for separation. In addition, the preparation method provided by the present disclosure has the advantages of simple and convenient operation of the entire route, low requirements for the equipment, high purity of the resultant product, and suitability for industrialized production.

Thirdly, the present disclosure performs structural analysis of the provided compound $S_p$-1 and confirms the chemical structure of the compound: the single crystal analysis determines the absolute configurations of phosphorus atom P1 (S), C9 (S), C18 (R), C19 (R), and C21 (R). The present disclosure also provides a brand new crystal of the compound $S_p$-1.

| Peak # | Name | Retention time | Area | Peak height | Area % |
|---|---|---|---|---|---|
| 1 | 61501b | 26.628 | 566450 | 82468 | 100 |
| Total | | | 566450 | 82468 | 100 |

Figure 2:
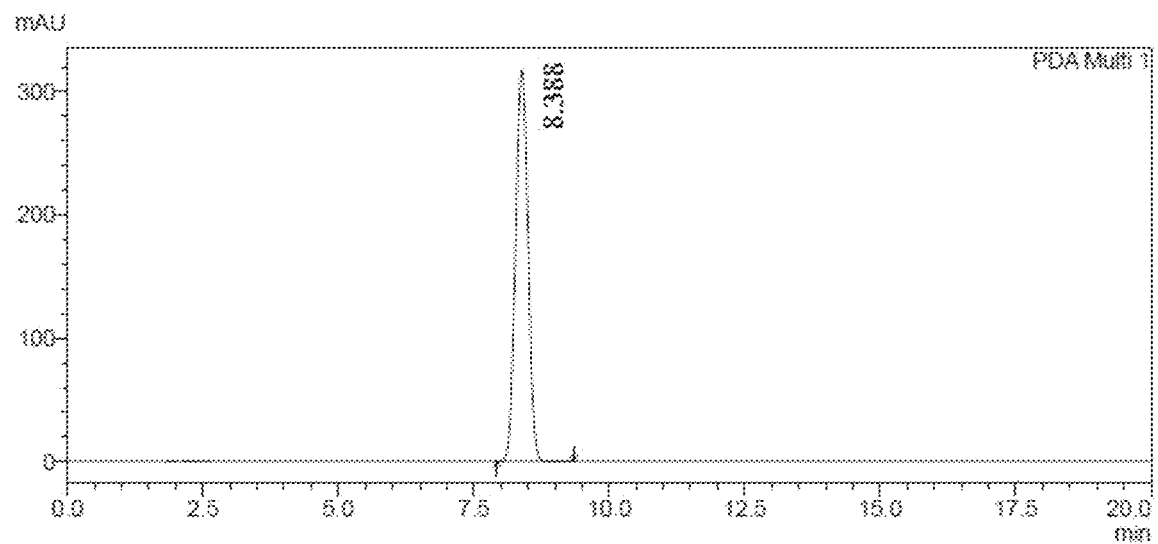

FIG. 2 shows an HPLC analysis chromatogram of the compound $S_p$-1 prepared according to the method of Example 5, wherein the HPLC purity of the compound $S_p$-1 is 100% and the peak data thereof is shown as below.

| Peak # | Retention time | Area | Peak height | Area % |
|---|---|---|---|---|
| 1 | 8.388 | 5096820 | 317635 | 100 |
| Total | | 5096820 | 317635 | 100 |

Figure 3:
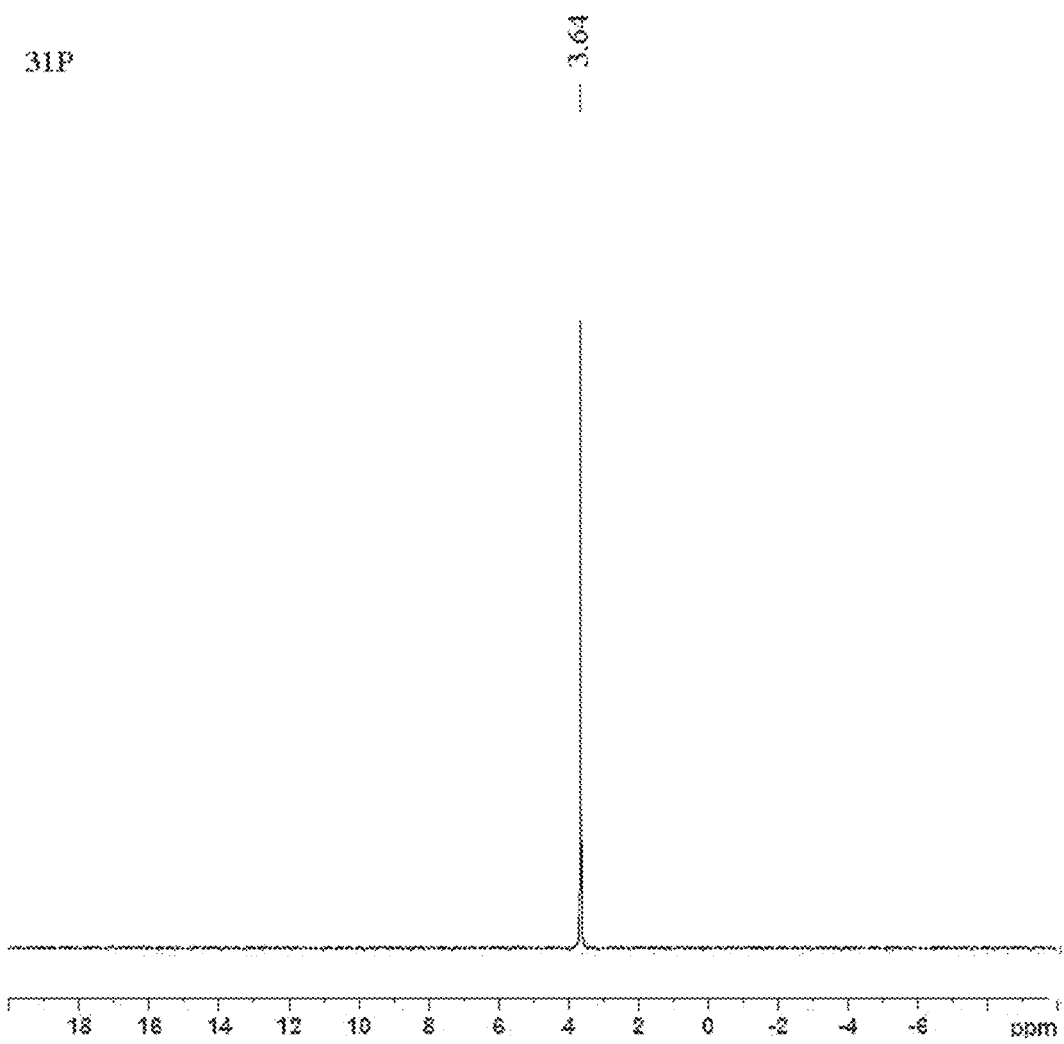

FIG. 3 shows a $^{31}$P-NMR spectrum of the compound $S_p$-1 prepared according to the method of Example 5, in which one peak is at $\delta_p$ 3.64.

Figure 4:
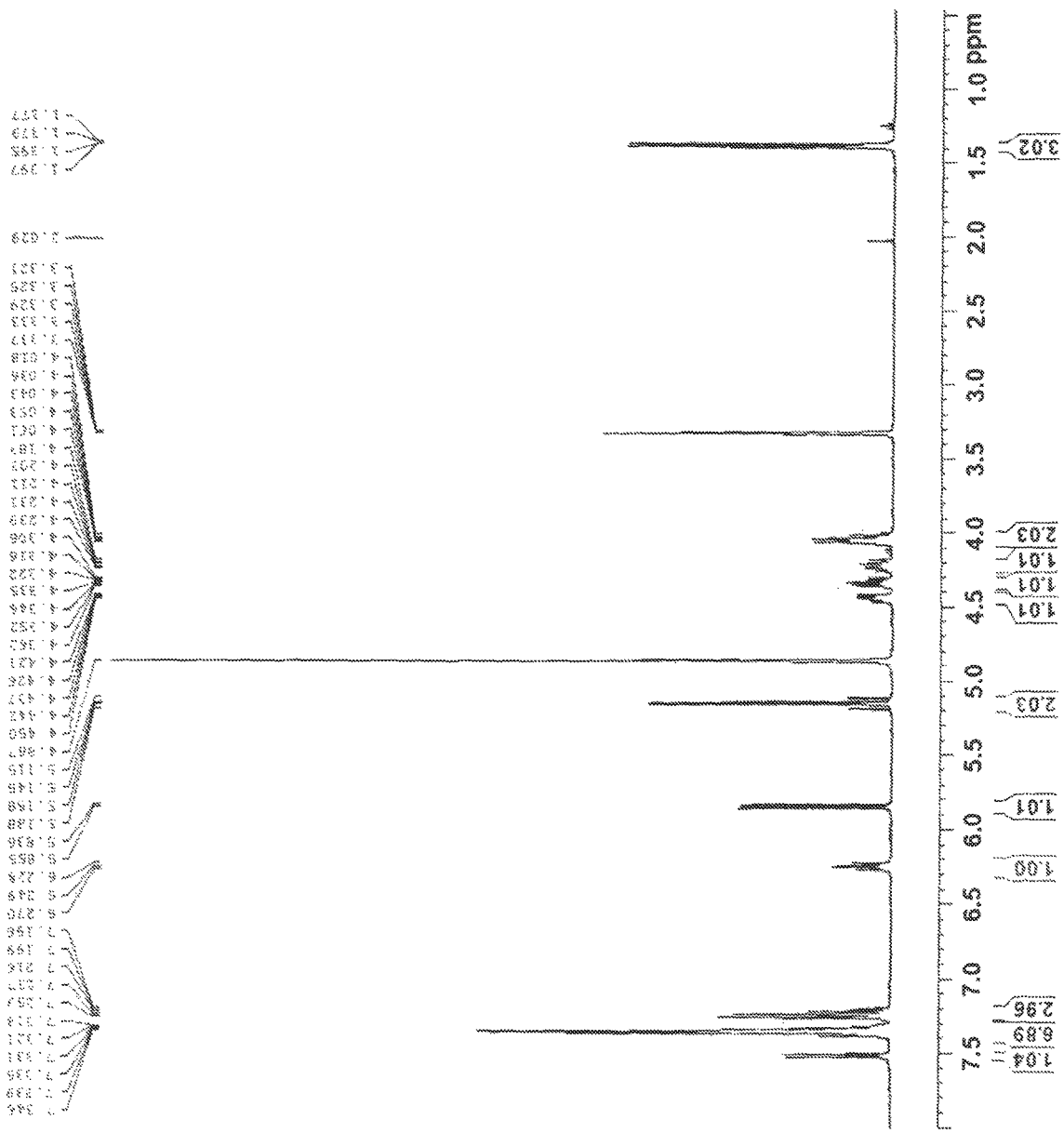

FIG. 4 shows an $^1$H-NMR spectrum of the compound $S_p$-1 prepared according to the method of Example 5.

Figure 5:
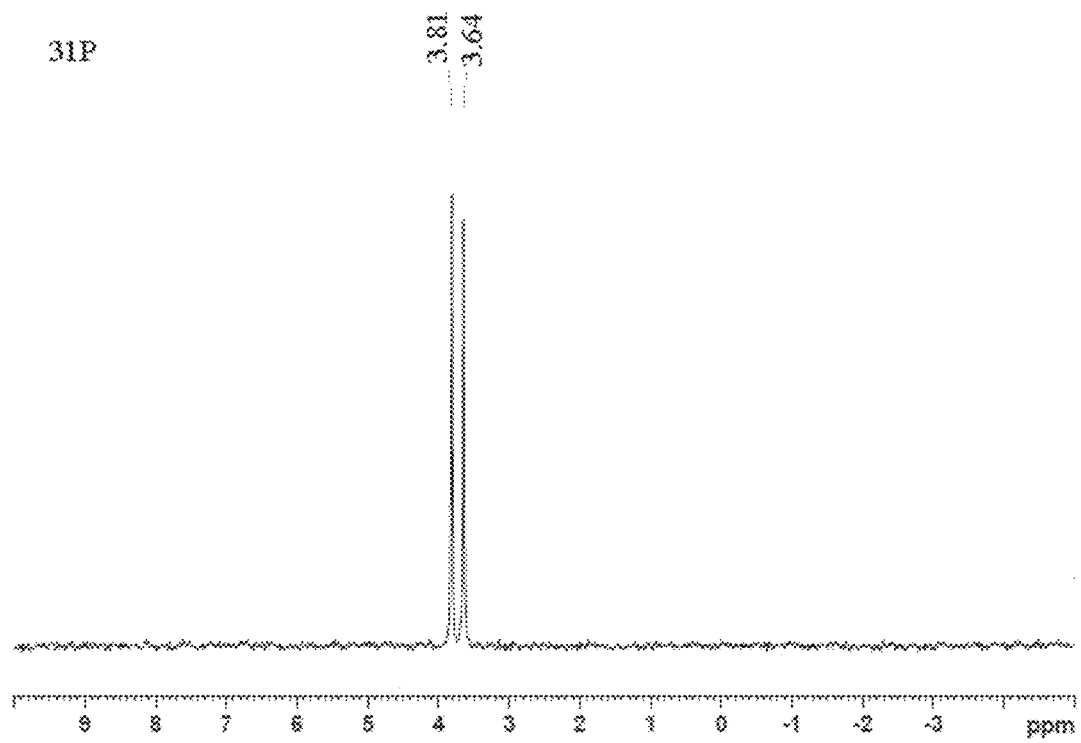

FIG. 5 shows a $^{31}$P-NMR spectrum of the compound 1 prepared according to the method of Comparative Example 2, in which two peaks are at $\delta_p$ 3.81, 3.64.

Figure 6:
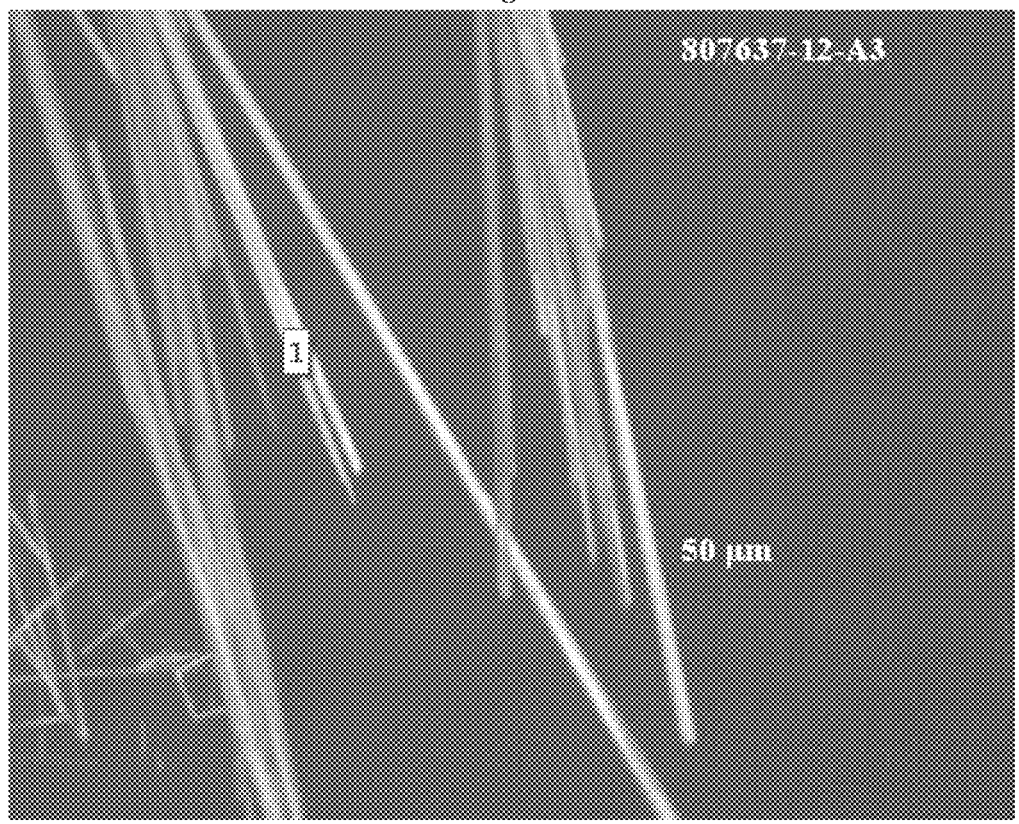

FIG. 6 shows a photomicrograph of the single crystal of the compound $S_p$-1.

Figure 7:
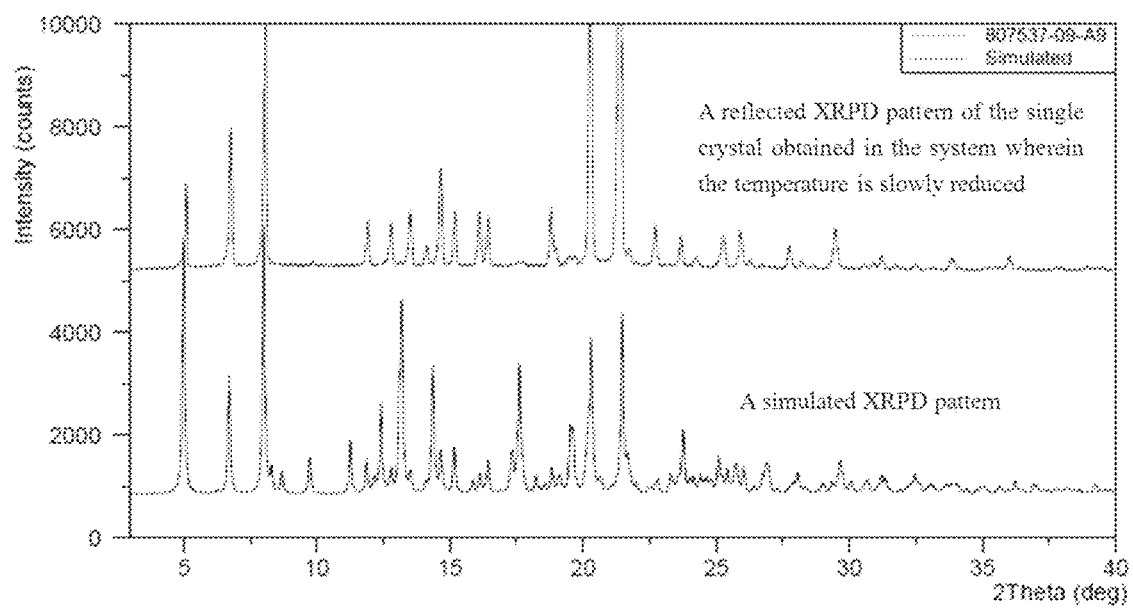

FIG. 7 shows a comparison diagram of the simulated XRPD of the single crystal of the compound $S_p$-1 with the reflected. XRPD of the single crystal.

Figure 8:
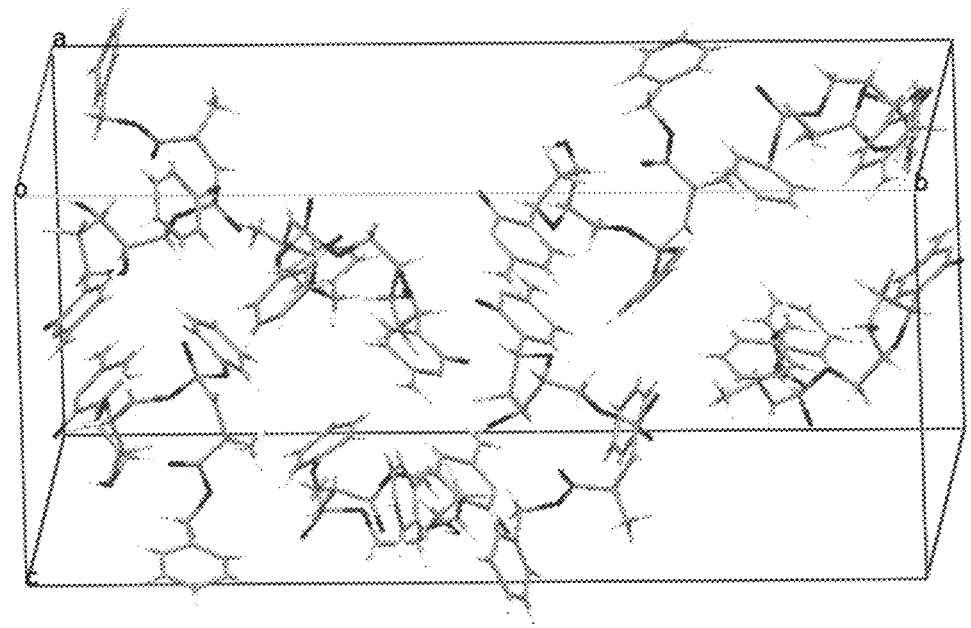

FIG. 8 shows a unit cell dimensions of the single crystal of the compound $S_p$-1.

Figure 9:
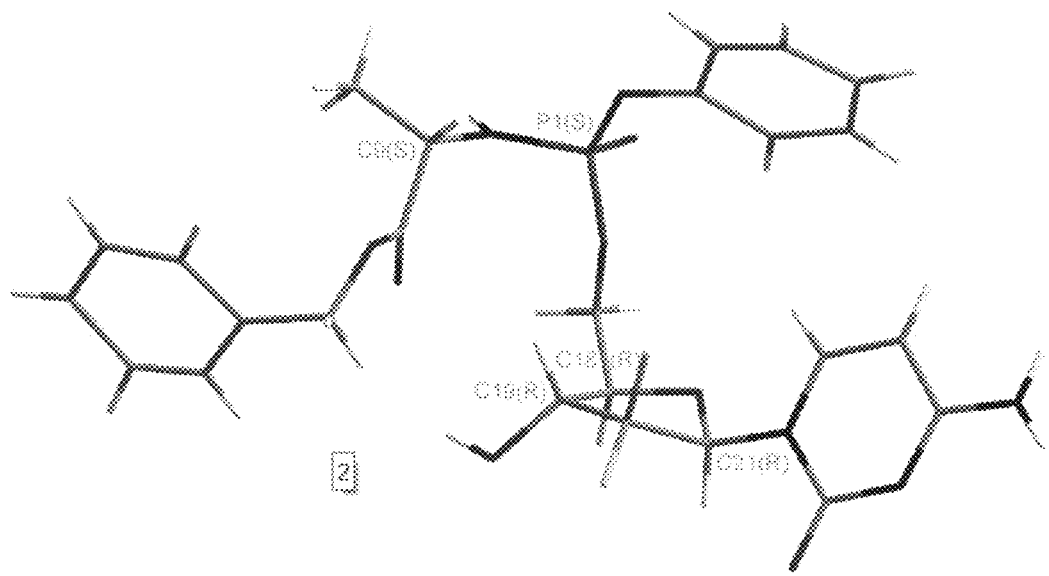

FIG. 9 shows a stereostructure diagram of the compound $S_p$-1.

Figure 10:
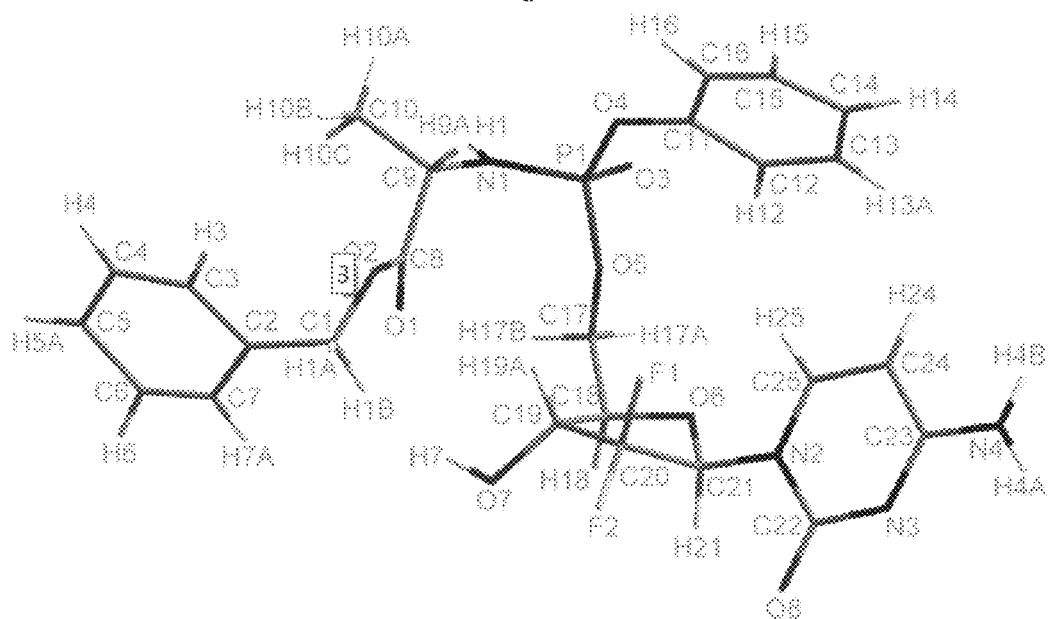

FIG. 10 shows a stereostructure diagram of the compound $S_p$-1.

Figure 11:
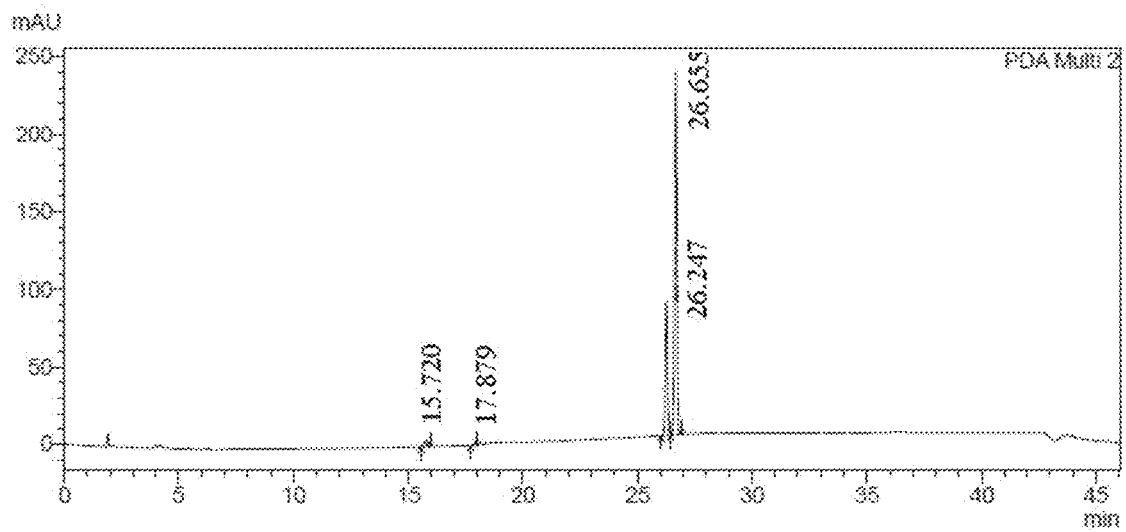

FIG. 11 shows an HPLC chromatogram of the compound 61502 used in the preparation of the compound 1 in Comparative Example 2, the ratio of the isomers thereof, i.e., 61501e to 61501b is 26.25%:72.03%.

Figure 12:
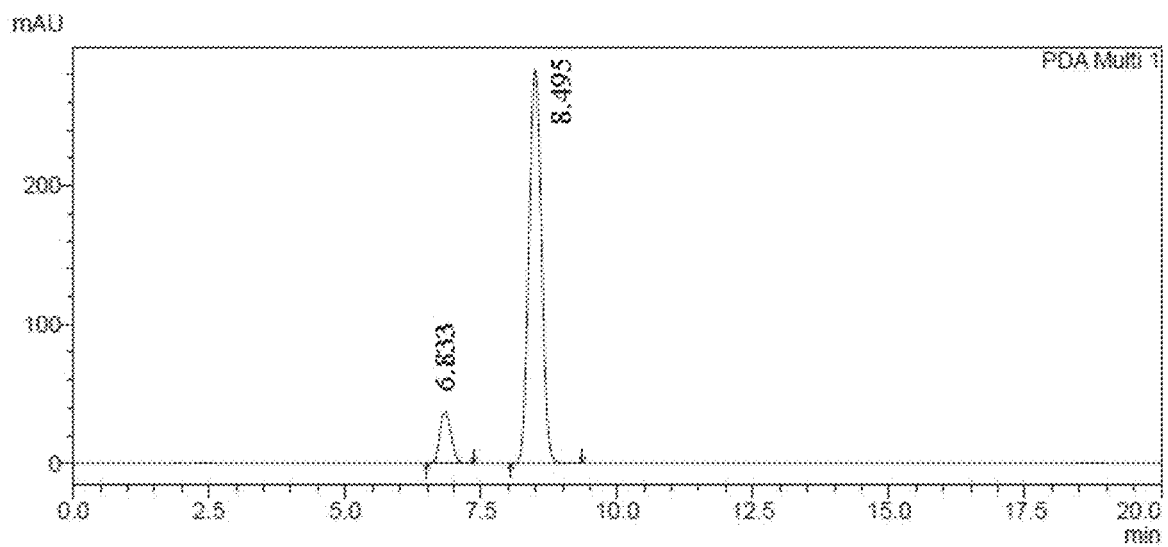

FIG. 12 shows an HPLC chromatogram of the compound 1 prepared according to the method of Comparative Example 2, the ratio of the isomers thereof, i.e., $R_p$-1 to $S_p$-1 is 10.82%:89.18%, and the peak data thereof is shown as below.

| Peak# | Name | Retention time | Area | Peak height | Area % |
|---|---|---|---|---|---|
| 1 | $R_p$-1 | 6.833 | 554365 | 37166 | 10.82 |
| 2 | $S_p$-1 | 8.495 | 4569402 | 283636 | 89.18 |
| Total | | | 5123768 | 320802 | 100 |

Figure 13:
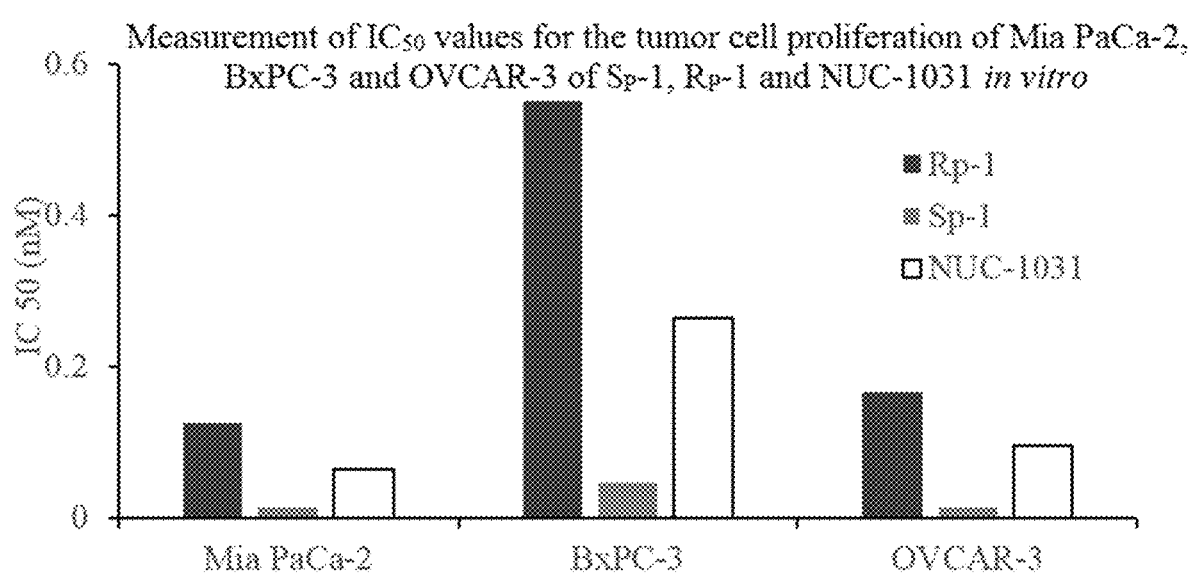

FIG. 13 shows the measured results of $IC_{50}$ values of the compound $S_p$-1, the compound $R_p$-1 and NUC-1031 for the tumor cell proliferation in vitro.

Figure 14:
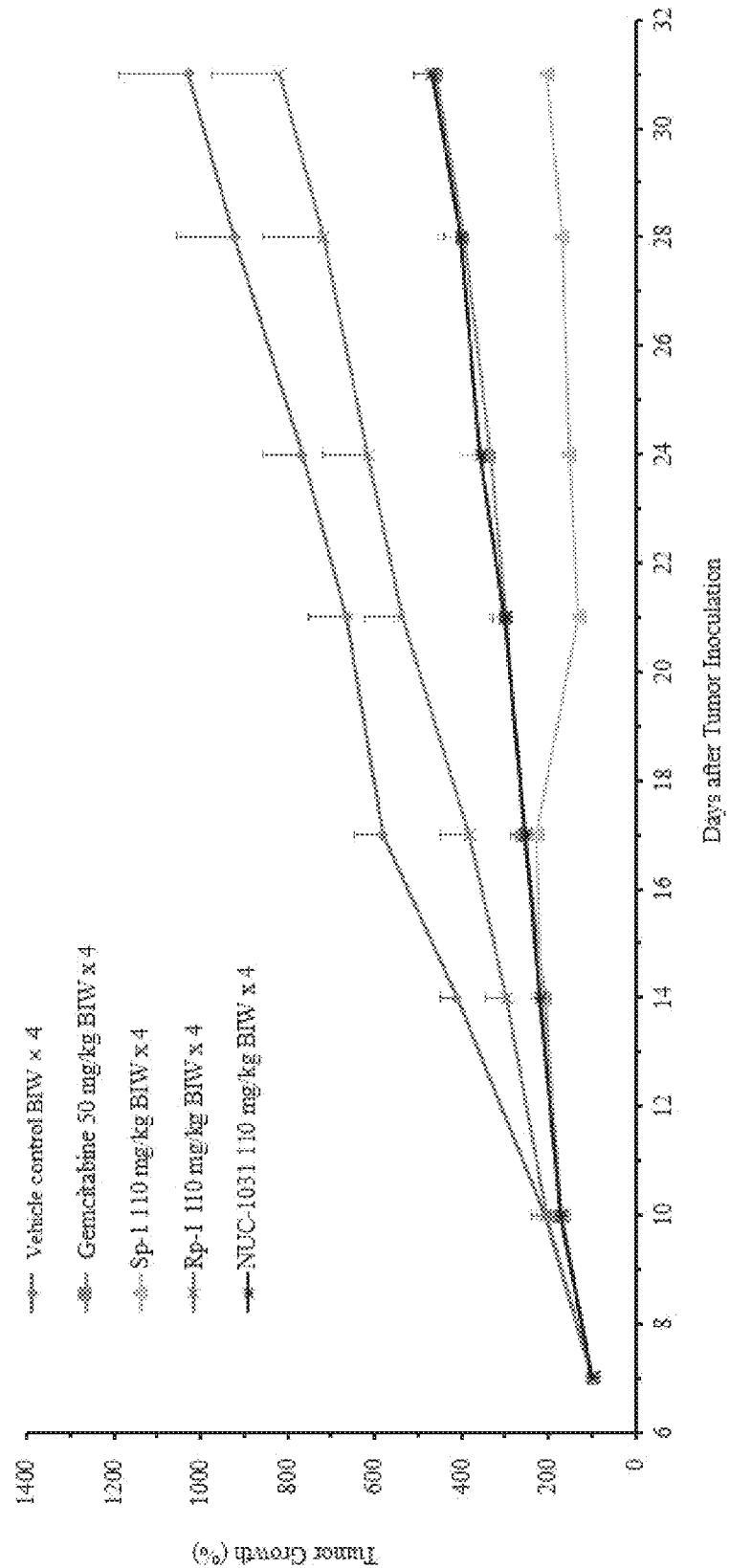

FIG. 14 shows the pharmacodynamic evaluation of the compound $S_p$-1, the compound $R_p$-1 and NUC-1031 in human pancreatic cancer subcutaneous xenograft mouse model.

Figure 15:
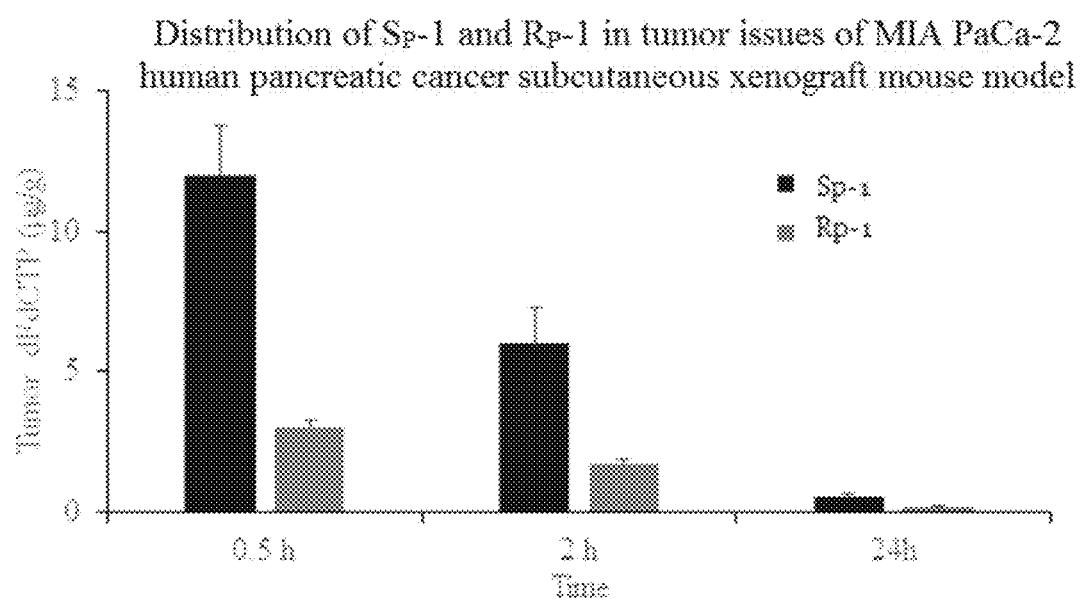

FIG. 15 shows the pharmacokinetic evaluation of the test drugs (the compound $S_p$-1 and the compound $R_p$-1) in MIA PaCa-2 human pancreatic cancer subcutaneous xenograft mouse model after single administration.

EXAMPLES

The contents of the present disclosure is further explained and described below in conjunction with the Examples. It should be understood that these Examples are merely used to describe the present disclosure but are not intended to limit the scope of the present disclosure. As for the experimental methods whose specific conditions are not indicated in the following Examples, the conditions are usually in accordance with the conventional conditions or the conditions suggested by the manufacturers. Unless otherwise specified, all percentages, rates, ratios, or parts are in terms of weight.

The photomicrograph of the sample of the single crystal is taken at room temperature using a stereo microscope PXS9-T (manufactured by Shanghai CeWei Photoelectric Technology Co. Ltd). The diffraction data of the single crystal is collected at 123(2) K using a Bruker D8 ADVANCE single crystal diffractometer (Mo Kα, λ=0.71073 Å).

The compound $R_p$-1 described in the test Examples of the present disclosure refers to a composition enriched in compound $R_p$-1, wherein the mass percentage of the compound $R_p$-1 is not less than 95% or more, and the used compound $S_p$-1 refers to the composition enriched in compound $S_p$-1 mentioned in the present disclosure, wherein the mass percentage of the compound $S_p$-1 is not less than 90%, and preferably not less than 99%. The compound $R_p$-1 can be obtained in a way similar to the preparation method of the compound $S_p$-1, except that the compound 61501e is obtained after the separation of the isomers of the compound 61502, and the compound 61501e is used in place of the compound 61501b to participate in the subsequent reactions to obtain the compound $R_p$-1.

The units of the percent weight in volume in the present disclosure are well known to those skilled in the art and the unit of the percent weight in volume refers to, for example, the weight of a solute in 100 milliliter of a solution. Unless otherwise defined, all the professional and scientific terms used herein have the same meanings as is familiar to one skilled in the art. In addition, any methods and materials similar or equivalent to the described contents can be used in the method of the present disclosure. The preferred embodiments and materials described herein are for illustrative purposes only.

In the present disclosure, the purity of the compound $S_p$-1 is determined by an HPLC method, which is conducted with the following column and conditions: octadecylsilane-bonded silica is used as a filler (YMC-hydrosphere C18 column, 150 mm×4.6 mm, 3 μm); a 0.1% phosphoric acid-methanol (10 to 50:90 to 50) serves as the mobile phase; the flow rate is 1.0 ml/min and the detection wavelength is 272 nm.

The purity of the intermediate compound 61501b of the present disclosure is also determined by an HPLC method, which is conducted with the following column and conditions: YMC hydrosphere 150 mm×4.6 mm, 3 μm; 40% to 85% methanol and 2‰ phosphoric acid/water are used as the mobile phases; run time: 46 min; gradient elution and adjusting the proportion of the mobile phase if necessary, flow rate: 1.0 (ml/min).

Example 1

Preparation of the Compound 61502

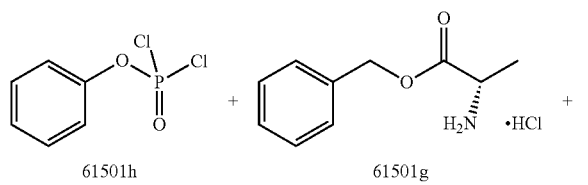

61501h    61501g

-continued

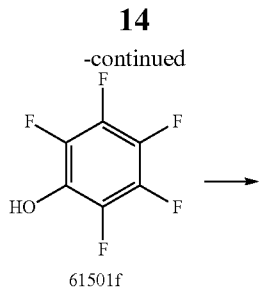

61501f

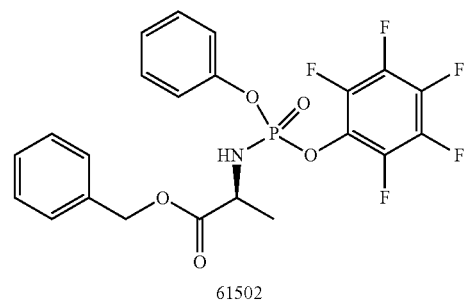

61502

To a solution of 61501h (20 g) in dichloromethane (60 ml) was added 20.6 g of 61501g at −80° C., and then 19.3 g of triethylamine (diluted in 20 ml of dichloromethane) was added. The mixture was stirred overnight at room temperature. To the mixture was added 61501f, followed by 19.3 g of triethylamine (diluted in 20 ml of dichloromethane), and the mixture was stirred at room temperature for 4 h. The mixture was directly deprived of the solvent, and the residue was dissolved in 200 ml of ethyl acetate and 400 ml of water; after ethyl acetate was separated, the aqueous phase was washed twice with ethyl acetate (2×100 ml), each time with 100 ml of ethyl acetate; the ethyl acetate phases were combined, washed with saline and dried with anhydrous sodium sulfate. Ethyl acetate was eliminated by distillation to give the target compound 61502, which was used directly in the subsequent purification.

Example 2

Preparation of the Compound 61501b

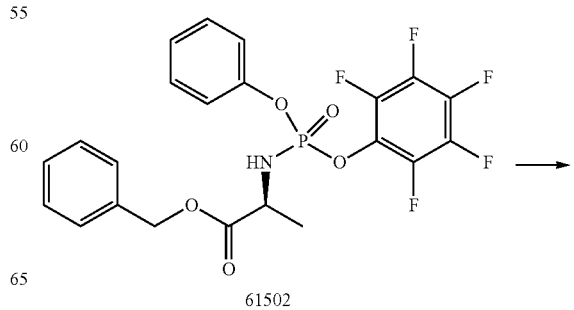

61502

-continued

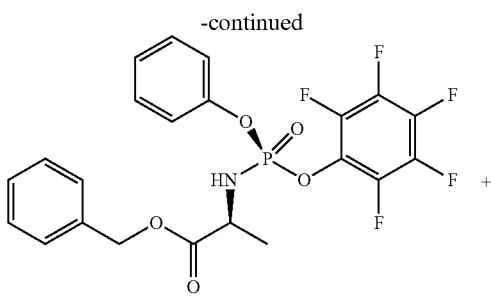

61501e

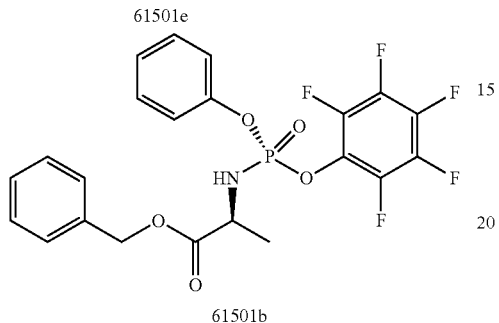

Figure 1:
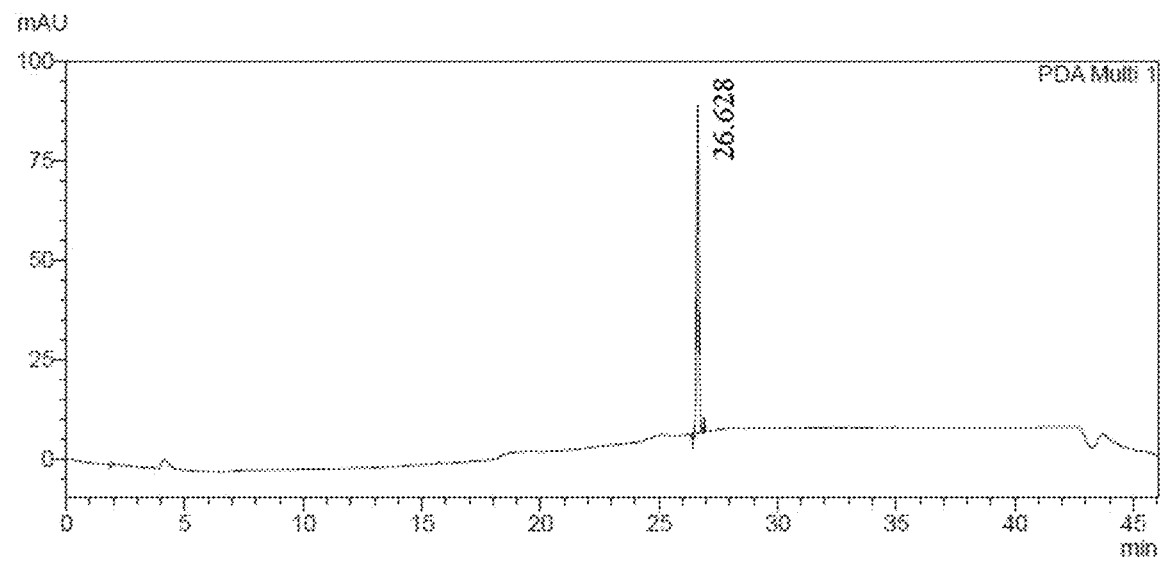
FIG. 1 shows an HPLC analysis chromatogram of the compound 61501b prepared according to the method of Example 2, wherein the HPLC purity of the compound 61501b is 100% and the peak data thereof is shown as below.

61501b 120 g of the compound 61502 was dissolved in 240 ml of ethyl acetate, and the mixture was stirred constantly; 720 ml of petroleum ether was added dropwise and slowly thereto at room temperature; crystals precipitated and the filtrate was removed by filtration to obtain 49.5 g of the compound 61501b in total with a yield of 41.2%; HPLC purity: 100% (as shown in FIG. 1).

Example 3

Preparation of the Compound 61501c

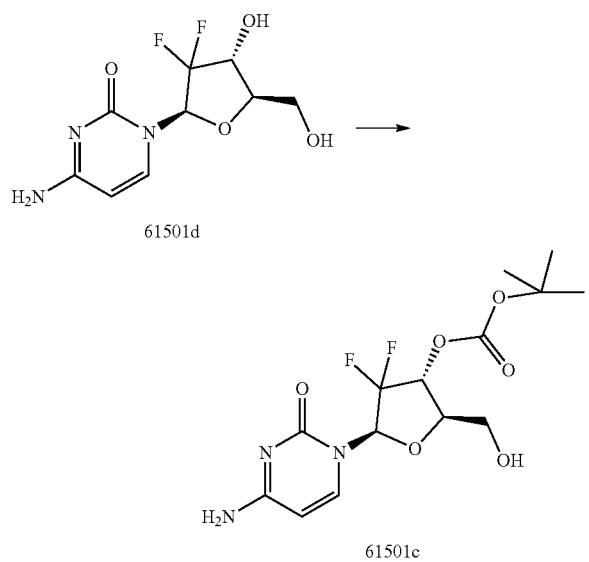

At room temperature, to a mixed solution of the compound 61501d (20 g) in tetrahydrofuran (200 ml) and water (100 ml) was added 35.4 g of sodium carbonate, followed by 17.5 g of di-tert-butyl dicarbonate, and the mixture was stirred at room temperature until the completion of the reaction. The mixture was subjected to extraction three times with ethyl acetate (3×200 ml), each time with 200 ml of ethyl acetate, and ethyl acetate was combined, washed with saline and dried with anhydrous sodium sulfate. After the solvent was eliminated by distillation, the residue was purified by silica gel chromatography (2.5% to 10% methanol/dichloromethane) to give 18 g of the compound 61501c with a yield of 67%.

Example 4

Preparation of the Compound 61501a

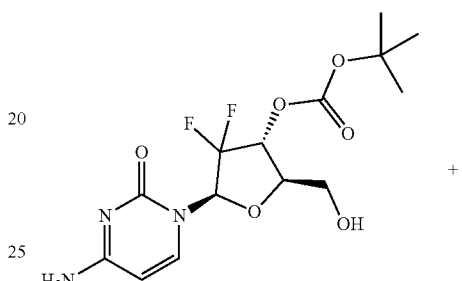

61501c

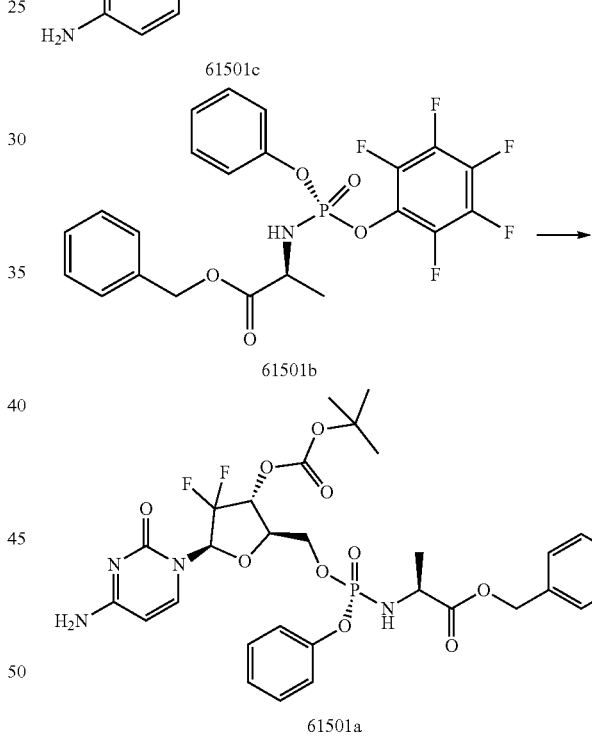

61501b

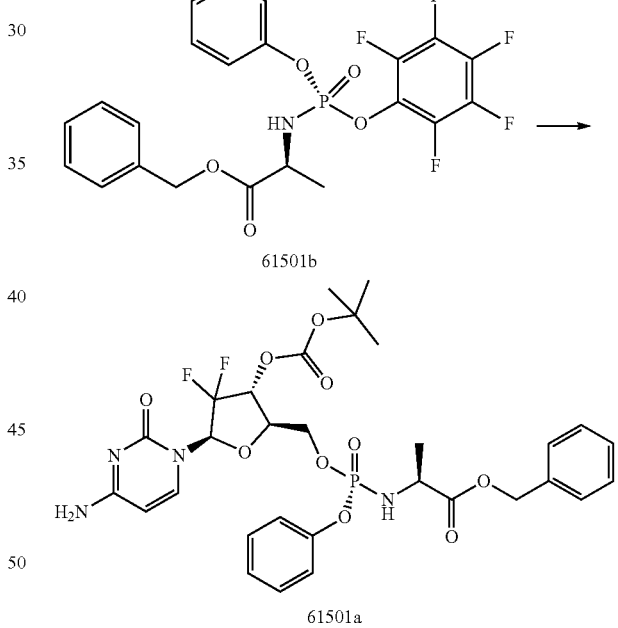

61501a

To a solution of the compound 61501c (5 g) in tetrahydrofuran (25 ml) was added 41.28 ml of a tert-butylmagnesium chloride solution having a concentration of 1.0 mol/L at 0° C.; after stirring and reacting for 1 h, 12.42 g of the compound 61501b obtained in Example 2 was added and stirred at room temperature till the reaction was complete. To the mixture was added 250 ml of a saturated aqueous solution of ammonium chloride and the aqueous phase was subjected to extraction three times with ethyl acetate (3×250 ml), each time with 250 ml of ethyl acetate; the ethyl acetate phases were combined, washed with saline, and dried with anhydrous sodium sulfate, and then the solvent was removed; purification by silica gel column chromatography (mobile phase: methanol/dichloromethane (the proportion of methanol increased from 2.5% to 5%), gradient elution) was performed to give 6.7 g of the compound 61501a with a yield of 71.3%, HPLC purity: 95.1%.

Example 5

Preparation of the Compound $S_p$-1

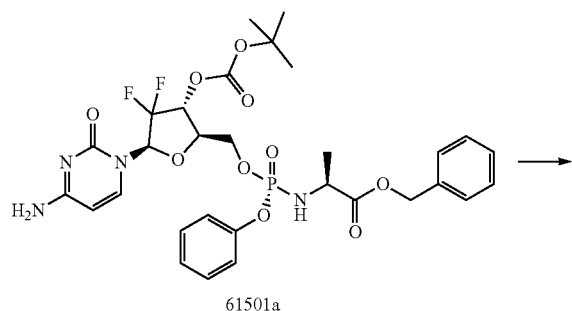

61501a

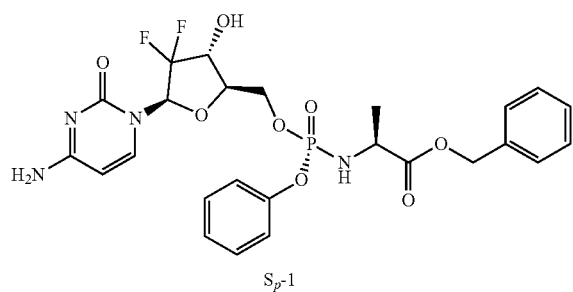

$S_p$-1

20.1 ml of trifluoroacetic acid was added to a solution of the compound 61501a (6.7 g) in dichloromethane (33.5 ml) at 0° C., and the mixture was stirred under heat preservation until the reaction was completed. After the mixture was deprived of the solvent, 150 ml of sodium bicarbonate solution was added, and the mixture was subjected to extraction three times with ethyl acetate, each time with 150 ml of ethyl acetate; the ethyl acetate phases were combined, washed with saline, and dried with anhydrous sodium sulfate; after the solvent was removed, purification by silica, gel column chromatography (mobile phase: methanol/dichloromethane (the proportion of methanol increased from 2.5% to 10%), gradient elution) was performed to give 4.1 g of the compound $S_p$-1 with a yield of 72%, HPLC purity: 100% (as shown in FIG. 2); $^{31}$P-NMR (202 MHz, MeOD): $\delta_p$ 3.64. (as shown in FIG. 3); $^1$-NMR (500 MHz, MeOD): $\delta_H$: 7.56, 7.52 (2d, J=7.5 Hz, 1H, H-6), 7.38-7.33 (m, 7H, ArH), 7.26-7.19 (m, 3H, ArH), 6.25 (apparent q, J=7.5 Hz, 1H, H-1'), 5.88, 5.84 (2×d, J=7.5 Hz, 1H, H-5), 5.18-5.12 (m, 2H, OCH$_2$Ph), 4.49-4.42 (m, 1H, H-5'), 4.38-4.31 (m, 1H, H-5'), 4.25-4.18 (m, 1H, H-3'), 4.07-4.01 (m, 2H, H-4', CHCH$_3$), 1.38 (apparent t, J=8.5 Hz, 3H, CHCH$_3$) (as shown in FIG. 4).

Example 6

Preparation of the Compound $S_p$-1

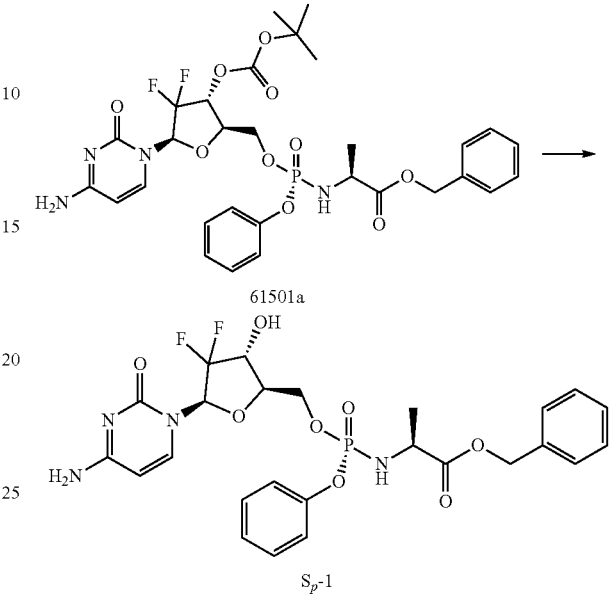

Hydrogen chloride/ethyl acetate (7 mol/L 6 ml) was added to a solution of the compound 61501a (2 g) in ethyl acetate (10 ml) at 0° C., and the mixture was stirred under heat preservation until the reaction was completed. After the solvent was removed by distillation, 50 ml of sodium bicarbonate solution was added and the mixture was subjected to extraction three times with ethyl acetate, each time with 50 ml of ethyl acetate. The ethyl acetate phases were combined, washed with saline and dried with anhydrous sodium sulfate; after the organic solvent was eliminated by distillation, the residue was purified by silica gel chromatography (mobile phase: methanol/dichloromethane (the proportion of methanol increased from 2.5% to 10%), gradient elution) to obtain 1225 mg of the compound $S_p$-1 with a yield of 70%, HPLC purity: 99.21%; $^{31}$P-NMR (202 MHz, MeOD): $\delta_p$ 3.64; $^1$H-NMR (500 MHz, MeOD): $\delta_H$: 7.56, 7.52 (2d, J=7.5 Hz, 1H, H-6), 7.38-7.33 (m, 7H, ArH), 7.26-7.19 (m, 3H, ArH), 6.25 (apparent q, J=7.5 Hz, 1H, H-1'), 5.88, 5.84 (2×d, J=7.5 Hz, 1H, H-5), 5.18-5.12 (m, 2H, OCH$_2$Ph), 4.49-4.42 (m, 1H, H-5'), 4.38-4.31 (m, 1H, H-5'), 4.25-4.18 (m, 1H, H-3'), 4.07-4.01 (m, 2H, H-4', CHCH$_3$), 1.38 (apparent t, J=8.5 Hz, 3H, CHCH$_3$).

Example 7

Preparation of the Compound $S_p$-1 in Crystalline Form

The compound $S_p$-1 prepared in Example 5 was added to a system of ethanol/water 1/3, v/v), and the temperature was gradually reduced from 50° C. to 5° C. at a rate of 0.01° C./min to obtain a rod-shaped single crystal (as shown in FIG. 6); the obtained single crystal was subjected to XRPD detection and the results were as shown in FIG. 7; the unit cell dimensions of the single crystal was as shown in FIG. 8; the absolute configuration of the molecule of the compound $S_p$-1: phosphorus atoms P1 (S), C9 (S), C18 (R), C19

(R), and C21 (R) was determined by single crystal analysis, and the stereostructure thereof was as shown in FIGS. 9 and 10.

Example 8

Preparation of the Compound $S_p$-1 in Crystalline Form

The compound $S_p$-1 prepared in Example 6 was added to a system of ethanol/water (1/3, v/v), and the temperature was gradually reduced from 30° C. to 0° C. to obtain the compound $S_p$-1 in crystalline form which was the same as that in Example 7.

Comparative Example 1

Preparation of the Compound 1

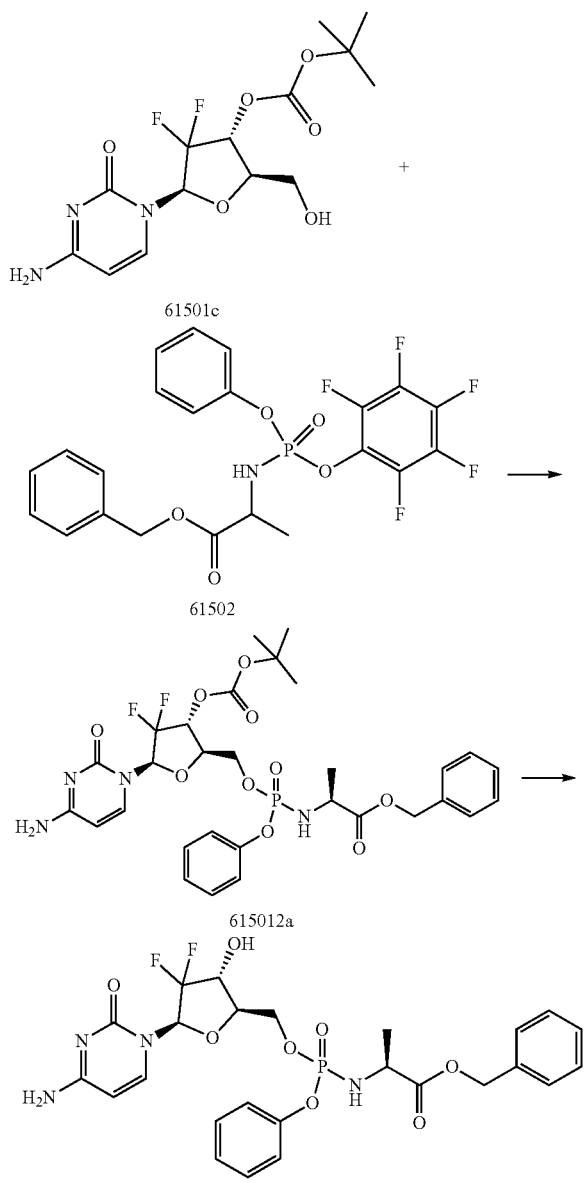

(1) Preparation of the Compound 615012a: to a solution of the compound 61501c (2 g) in tetrahydrofuran (10 ml) was added a solution of tert-butylmagnesium chloride (1.0 mol/L, 16 ml) at 0° C.; after stirring and reacting for 1 h, the compound 61502 (5 g) (wherein the ratio of the isomers, i.e., 61501e to 61501b was 26.25%:72.03%, as shown in FIG. 11) was added, and the mixture was stirred at room temperature until the completion of the reaction. 50 ml of water was added to the mixture and the aqueous phase was subjected to extraction three times with ethyl acetate (3×100 ml), each time with 100 ml of ethyl acetate; the ethyl acetate phases were combined, washed with saline and dried with anhydrous sodium sulfate; and the solvent was removed. Purification by silica gel column chromatography (eluent: methanol/dichloromethane: 2.5% to 5%, gradient elution) was performed to give 1.9 g of the compound 615012a with a yield of 53%.

(2) Preparation of the Compound 1: 12 ml of trifluoroacetic acid was added to a solution of the compound 615012a (3.98 g) in dichloromethane (10 ml) at 0° C., and the mixture was stirred under heat preservation until the reaction was completed. After the mixture was deprived of the solvent, 100 ml of sodium bicarbonate solution was added, and the mixture was subjected to extraction three times with ethyl acetate, each time with 80 ml of ethyl acetate; the ethyl acetate phases were combined, washed with saline, and dried with anhydrous sodium sulfate; after the solvent was removed, several purifications by silica gel column chromatography (mobile phase: methanol/dichloromethane (the proportion of methanol increased from 2.5% to 10%), gradient elution) were performed to give 1.1 g of the compound 1, HPLC purity: 100%; wherein the ratio of the isomers, i.e., $R_p$-1 to $S_p$-1 was 10.82%:89.18% (as shown in FIG. 12); $^{31}$P-NMR (202 MHz, MeOD): $\delta_p$3.81, 3.64, where $\delta_p$ 3.81 is the absorption peak of $^{31}$P in the isomer $R_p$-1, and $\delta_p$ 3.64 is the absorption peak of $^{31}$P in the isomer $S_p$-1.

Determination of Pharmacological Activity:

Example 9

Measurement of $IC_{50}$ Values for the Tumor Cell Proliferation In Vitro

The 50% inhibitory concentrations ($IC_{50}$) for the cell proliferation of the compound $S_p$-1, the compound $R_p$-1 and NUC-1031 in BxPC-3, MIA PaCa-2 and OVCAR-3 tumor cell lines were measured using the CTG method.

Cells in an exponential growth phase were collected and the viable cells were counted using a Vi-Cell XR cell counter. The cell suspension was adjusted to 3.33×10⁴/ml or 5.56×10⁴/ml with culture media corresponding to the respective cells. 90 μl of cell suspension was added to each well of a 96-well cell culture plate, and the final cell concentrations of BxPC-3 and MIA PaCa-2 were 3000 cells/well and the final cell concentration of OVCAR-3 was 5000 cells/well. Each test compound was dissolved in DMSO to become 10 mM stock solutions. 3.16× serial dilutions were prepared by the stock solutions and DMSO. Then the dilutions were respectively diluted 100 times with the culture media. Finally, to each well of the respective cell lines was added 10 μl of the corresponding 10-fold solution, triplicate wells were set up for each drug concentration (see the methods for formulating the compounds and the design of sample adding: the plate map for $IC_{50}$ determination); for the concentration ranges of the test compounds and the reference compounds used for the final tests, please see the methods for formulating the compounds and the design of sample adding on the following pages: the test compounds and the reference compounds were diluted, and the final concentration of DMSO in each well was 0.1%. The cells were placed in an incubator at 37° C. with 5% $CO_2$ to be cultured for 72 hours (BxPC-3, MIA PaCa-2) or 96 hours (OVCAR-3). After 72 or 96 hours of drug treatment, 50 µl (½ culture volume) of CTG solution, which had been melted and equilibrated to room temperature in advance was added to each well according to the operating instruction of CTG; the mixtures were mixed evenly for 2 minutes with a microwell plate shaker, placed at room temperature for 10 minutes, and then an Envision 2104 plate reader was used to measure the values of the fluorescence signals.

Cell viability was calculated with the formula: $V_{sample}/V_{vehicle\ control} \times 100\%$, wherein $V_{sample}$ is the reading of the treatment group and $V_{vehicle\ control}$ is the average value of the vehicle control group. Non-linear regression model was used to plot the S-shape dose-survival rate curves and calculate the $IC_{50}$ values using GraphPad Prism 5.0 software. The $IC_{50}$ values of the tested compounds against the three cell lines are shown in Table 1 below.

TABLE 1

$IC_{50}$ Values of the Tested Compounds against the three Cell Lines

| Cell line | Compound ($S_P$-1) | | Compound ($R_P$-1) | | NUC-1031 | |
| --- | --- | --- | --- | --- | --- | --- |
| | $IC_{50}$ (nM) | Max inh. (%) | $IC_{50}$ (nM) | Max inh. (%) | $IC_{50}$ (nM) | Max inh. (%) |
| BxPC-3 | 0.045 | 66.48 | 0.554 | 61.54 | 0.263 | 65.82 |
| MIA PaCa-2 | 0.012 | 71 | 0.126 | 69.2 | 0.063 | 65.03 |
| OVCAR-3 | 0.013 | 58.22 | 0.167 | 54.19 | 0.095 | 56.3 |

2.5% HS. MIA PaCa-2 cells in an exponential growth phase were collected and resuspended in PBS to a suitable concentration for the subcutaneous tumor inoculation in nude mice.

Animal modeling and Grouping: BALB/c nude mice, female, 6 to 8 weeks old (the predicted weeks of age of the mice when being inoculated with tumor cells), 18 to 22 g, purchased from Shanghai Lingchang Biological Technology Co., LTD. A total of 52 mice (40 plus 30% surplus) were required. After grouping, there were 5 groups in total, each group having 8 mice. All experimental mice were raised in a barrier system and adapted to the environment for at least 7 days in advance. Each mice was subcutaneously inoculated with $3 \times 10^6$ MIA PaCa-2 cells on the right back and the cells were resuspended in PBS and matrigel (1:1) (0.1 ml/mice); the tumor growth was observed regularly, and when the tumor volumes reached an average size of 150 to 200 $mm^3$, the mice were randomly divided into groups according to the size of tumor and body weight of the mice, and the drugs were administered. Detailed administration methods, administration doses and administration routes were shown in Table 2.

TABLE 2

Administration Routes, Doses and Strategies of the Test Drugs in the MIA PaCa-2 Animal Model

| Group | Number of animals | Treatment group | Dose (mmoL/kg) | Dose (mg/kg) | Volume of administration (µl/g) | Means of administration | Treatment cycle |
| --- | --- | --- | --- | --- | --- | --- | --- |
| 1 | 8 | Vehicle control | — | — | 10 | i.p. | BIW × 4 |
| 2 | 8 | Gemcitabine | 0.19 | 50 | 10 | i.p. | BIW × 4 |
| 3 | 8 | Compound $S_P$-1 | 0.19 | 110 | 10 | i.p. | BIW × 4 |
| 4 | 8 | Compound $R_P$-1 | 0.19 | 110 | 10 | i.p. | BIW × 4 |
| 5 | 8 | NUC-1031 | 0.19 | 110 | 10 | i.p | BIW × 4 |

Note:
i.p.: administered by intraperitoneal injection;
BIW: administered twice a week;

The above experimental results showed that the compound $S_p$-1, the compound $R_p$-1 and NUC-1031 all exhibited relatively strong cytotoxic effect on BxPC-3, MIA PaCa-2 and OVCAR-3 tumor cells with the $IC_{50}$ values within about 0.01 nM to 1 nM; the inhibitory effect of the compound $S_p$-1 on the proliferation activity of tumor cells in vitro was about 10 times that of the compound $R_p$-1, which was also shown in FIG. 13.

Example 10

Pharmacodynamic Evaluation of the Test Drugs: the Compound $S_p$-1, the Compound and NUC-1031 in Human Pancreatic Cancer Subcutaneous Xenograft Mouse Model Cell Culture: MIA PaCa-2 cells were cultured in a DMEM culture medium containing 10% fetal bovine serum and Experimental Observation Index and Calculation:

Relative tumor inhibition rate TGI(%): TGI %=(1−T/C)× 100%. T/C % is the relative tumor growth rate, which is the percentage of the relative tumor volume or tumor weight of the treatment groups with respect to the control group at a certain timepoint. T and C are the relative tumor volume (RTV) or tumor weight (TW), respectively, of the treatment groups and the control group at a particular timepoint.

The calculation formula is as follows: T/C %=$T_{RTV}/C_{RTV} \times 100\%$ ($T_{RTV}$: the average RTV of a treatment group; $C_{RTV}$: the average RTV of the vehicle control group; RTV=$V_t/V_0$, $V_0$ is the tumor volume of an animal at the time of grouping, $V_t$ is the tumor volume of an animal after treatment). Or T/C %=$T_{TW}/C_{TW} \times 100\%$ ($T_{TW}$: the average tumor weight of a treatment group at the end of the experiment; $C_{TW}$: the average tumor weight of the vehicle control group at the end of the experiment).

Experimental Results:

Administration of gemcitabine twice a week for 4 consecutive weeks had good inhibitory effect on tumor, with a relative tumor inhibition rate of 55%. TGIs (%) obtained after the administration of the compound $S_p$-1, the compound $R_p$-1 and NUC-1031 at an equimolar dose of gemcitabine twice a week for 4 consecutive weeks were 79%, 22% and 54%, respectively. The results showed that the compound $S_p$-1 had better in vivo anti-tumor activity than the compound $R_p$-1 (as shown in FIG. 14).

Example 11

Pharmacokinetic Evaluation of the Test Drugs: the Compound $S_p$-1 and the Compound $R_p$-1 in MIA PaCa-2 Human Pancreatic Cancer Subcutaneous Xenograft Mouse Model after Single Administration Cell Culture: MIA PaCa-2 cells were cultured in a DMEM culture medium containing 10% fetal bovine serum and 2.5% HS. MIA PaCa-2 cells in an exponential growth phase were collected and resuspended in PBS to a suitable concentration for the subcutaneous tumor inoculation in nude mice.

Animal modeling and Grouping: BALB/c nude mice, female, 6 to 8 weeks old (the predicted weeks of age of the nice when being inoculated with tumor cells), 18 to 22 g, purchased from Shanghai Lingchang Biological Technology Co., LTD. A total of 47 mice (36 plus 30% surplus) were required. After grouping, there were 6 groups in total, each group having 6 mice. All experimental mice were raised in a barrier system and adapted to the environment for at least 7 days in advance. Each mice was subcutaneously inoculated with $3 \times 10^6$ MIA PaCa-2 cells on the right back and the cells were resuspended in PBS and matrigel (1:1) (0.1 ml/mice); the tumor growth was observed regularly, and when the tumor volumes reached an average size of 200 to 250 mm³, the mice were randomly divided into groups according to the size of tumor and body weight of the mice, and the drugs were administered. Detailed administration methods, administration doses and administration routes were shown in Table 3.

Tumor tissues were collected at 0.5 h, 2 h and 24 h respectively after administration; the tumors were quickly frozen in liquid nitrogen immediately after being collected, and then the tumor weights were measured; the tumors were homogenized in 20% methanol/water under an ice bath at a ratio of 1:5 and the concentration of dFdCTP, an active metabolite in tumor tissue, was determined by LC-MS/MS.

Experimental Results:

The experimental results obtained after the administration of 110 mg/kg of the compound SP-1 and the compound RP-1 by intraperitoneal injection were shown in FIG. 15. The concentrations of dFdCTP, an active metabolite in tumor tissue at 0.5, 2 and 24 hours after the intraperitoneal injection of the compound SP-1 were 12.0, 5.97 and 0.504 µg/g, respectively, and the concentrations of dFdCTP, an active metabolite in tumor tissue at 0.5, 2 and 24 hours after the intraperitoneal injection of the compound RIP-1 were 3.03, 1.67 and 0.157 µg/g, respectively. The concentrations of dFdCTP, an active metabolite in tumor tissue at 0, 5, 2 and 24 hours after the administration of compound SP-1 were respectively 3.96, 3.57 and 3.21 times those of the compound RP-1 (as shown in FIG. 15).

What is claimed is:

1. A method for preparing the compound of formula $S_p$-1, wherein said method comprises:

reacting a compound 61501b with a compound 61501c to prepare a compound 61501a:

TABLE 3

Administration Routes, Doses and Strategies of the Test Drugs in the MIA PaCa-2 Animal Model

| Group | Number of animals | Treatment group | Dose (mmoL/kg) | Dose (mg/kg) | Volume of administration (µl/g) | Means of administration | Timepoint of resecting tumor after single administration |
|---|---|---|---|---|---|---|---|
| 1 | 6 | Compound $S_P$-1 | 0.19 | 110 | 10 | i.p. | 0.5 h |
| 2 | 6 | Compound $S_P$-1 | 0.19 | 110 | 10 | i.p. | 2 h |
| 3 | 6 | Compound $S_P$-1 | 0.19 | 110 | 10 | i.p. | 24 h |
| 4 | 6 | Compound $R_P$-1 | 0.19 | 110 | 10 | i.p. | 0.5 h |
| 5 | 6 | Compound $R_P$-1 | 0.19 | 110 | 10 | i.p. | 2 h |
| 6 | 6 | Compound $R_P$-1 | 0.19 | 110 | 10 | i.p. | 24 h |

Note:
i.p.: administered by intraperitoneal injection;
BIW: administered twice a week;

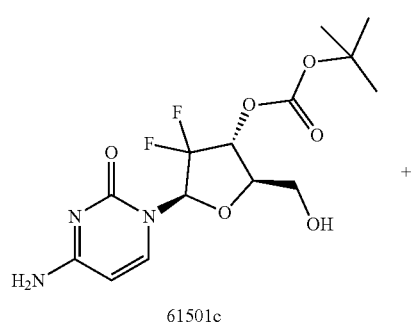

61501c

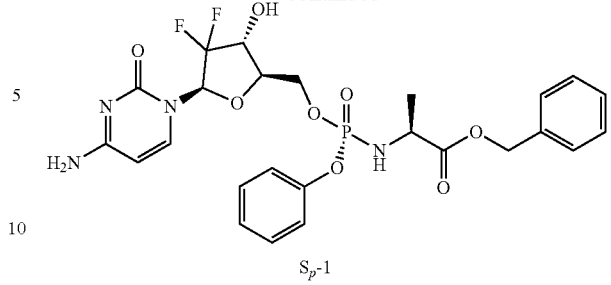

2. The method according to claim 1, wherein said method comprises isolating the compound 61501b by crystallization of a compound 61502:

61501b and, deprotecting the hydroxyl protecting group of the compound 61501a to obtain the compound Sp-1:

61501a

61502

61501e

61501b

3. The method according to claim 2, wherein said method comprises reacting a compound 61501h with a compound 61501g under alkaline conditions, and then reacting with a compound 61501f to prepare the compound 61502, 61501h   61501g 61501a -continued

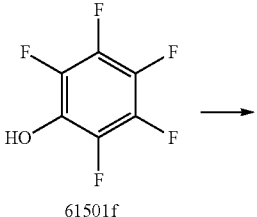
61501f

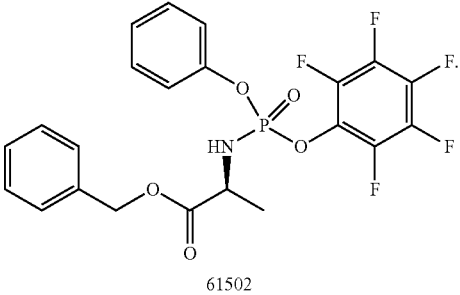
61502

4. The method according to claim 1, wherein the compound 61501c is prepared by reacting a compound 61501d with di-tert-butyl dicarbonate

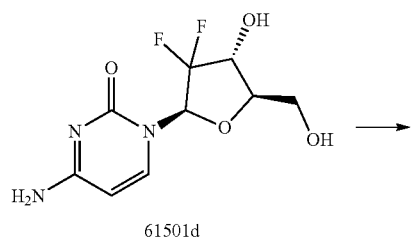
61501d

-continued

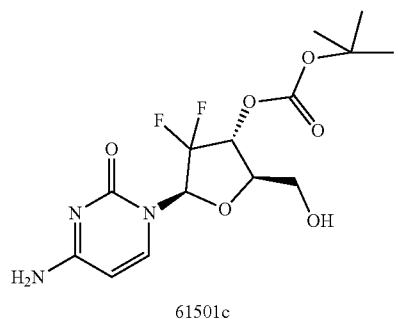
61501c

5. The method according to claim 2, wherein the crystallization solvent is ethyl acetate/petroleum ether.

6. The method according to claim 5, wherein the weight-to-volume ratio of the compound 61502 to ethyl acetate is 2:5 to 4:5, and the volume ratio of ethyl acetate to petroleum ether is 1:4 to 1:6.

7. The method according to claim 1, wherein the purity of the prepared compound Sp-1 is not less than 90%.

8. The method according to claim 7, wherein the purity of the prepared compound Sp-1 is not less than 99%.

9. The method according to claim 1, wherein said method further comprises crystalizing the compound Sp-1 from a solvent, wherein the solvent is consists of a lower alcohol and water.

10. The method according to claim 9, wherein the solvent is consists of 1 part of $C_{1-3}$ alcohol and 3 parts of water.

* * * * *